(12) United States Patent
Maeda et al.

(10) Patent No.: US 9,029,434 B2
(45) Date of Patent: May 12, 2015

(54) COLORED PHOTOSENSITIVE COMPOSITION

(71) Applicant: Adeka Corporation, Arakawa-ku (JP)

(72) Inventors: Yosuke Maeda, Tokyo (JP); Masaaki Shimizu, Tokyo (JP); Koichi Shigeno, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 14/337,644

(22) Filed: Jul. 22, 2014

(65) Prior Publication Data

US 2014/0332737 A1 Nov. 13, 2014

Related U.S. Application Data

(62) Division of application No. 13/990,433, filed as application No. PCT/JP2011/080233 on Dec. 27, 2011.

(30) Foreign Application Priority Data

Jan. 25, 2011 (JP) .................................. 2011-012991

(51) Int. Cl.
| | |
|---|---|
| C08F 2/50 | (2006.01) |
| C08F 2/48 | (2006.01) |
| B29C 71/04 | (2006.01) |
| A61L 24/00 | (2006.01) |
| C08G 61/04 | (2006.01) |
| G02B 5/23 | (2006.01) |
| C07D 295/14 | (2006.01) |
| G02B 5/22 | (2006.01) |
| C09B 23/10 | (2006.01) |
| C09B 23/14 | (2006.01) |
| G03F 7/00 | (2006.01) |
| G03C 1/73 | (2006.01) |
| C09B 69/10 | (2006.01) |
| G02B 1/04 | (2006.01) |
| G03F 7/027 | (2006.01) |
| G03F 7/105 | (2006.01) |

(52) U.S. Cl.
CPC ................ *G02B 5/23* (2013.01); *C07D 295/14* (2013.01); *G02B 5/223* (2013.01); *C09B 23/105* (2013.01); *C09B 23/143* (2013.01); *G03F 7/0007* (2013.01); *G03C 1/733* (2013.01); *C09B 23/141* (2013.01); *C09B 69/105* (2013.01); *C09B 69/109* (2013.01); *G02B 1/04* (2013.01); *G03F 7/027* (2013.01); *G03F 7/105* (2013.01)

(58) Field of Classification Search
USPC ............. 522/39, 33, 6, 1, 71, 189, 184; 520/1
See application file for complete search history.

(56) References Cited

U.S. PATENT DOCUMENTS

| | | | |
|---|---|---|---|
| 2,766,233 A | 10/1956 | Kartinos et al. | |
| 3,850,960 A | 11/1974 | Avar et al. | |
| 4,749,774 A | 6/1988 | Weaver et al. | |
| 4,826,903 A | 5/1989 | Weaver et al. | |
| 4,925,782 A | 5/1990 | Okada et al. | |
| 4,958,043 A * | 9/1990 | Weaver et al. | ................ 558/403 |
| 5,106,942 A | 4/1992 | Krutak et al. | |
| 5,347,394 A | 9/1994 | Wakita et al. | |
| 2003/0031691 A1 | 2/2003 | Richard et al. | |
| 2005/0008588 A1 | 1/2005 | Candau et al. | |
| 2007/0184366 A1* | 8/2007 | Takakuwa | ......................... 430/7 |

FOREIGN PATENT DOCUMENTS

| | | |
|---|---|---|
| JP | 63-172717 | 7/1988 |
| JP | 2-292371 | 12/1990 |
| JP | 03-53987 | 3/1991 |
| JP | 3-502814 | 6/1991 |
| JP | 3-261182 | 11/1991 |
| JP | 4-505032 | 9/1992 |
| JP | 6-222410 | 8/1994 |
| JP | 8-081635 | 3/1996 |
| JP | 8-081636 | 3/1996 |
| JP | 08-109335 | 4/1996 |
| JP | 11-084695 | 3/1999 |
| JP | 2003-095909 | 4/2003 |
| JP | 2005-002112 | 1/2005 |
| JP | 2005-088210 | 4/2005 |
| JP | 2007-286189 | 11/2007 |
| JP | 2009-016158 | 1/2009 |
| WO | WO 89/10349 | 11/1989 |

OTHER PUBLICATIONS

International Search Report, PCT/JP2011/080233, Feb. 7, 2012.

* cited by examiner

*Primary Examiner* — Ling Choi
*Assistant Examiner* — Jessica E Whiteley
(74) *Attorney, Agent, or Firm* — Young & Thompson

(57) ABSTRACT

The present invention provides a dye that is excellent in solubility and heat-resistance, and a novel compound that is suitable for the dye, and specifically provides a yellow dye having a maximum absorption wavelength in the region of 420 to 470 nm. Furthermore, the present invention provides a colored (alkali-developable) photosensitive composition and an optical filter using the dye, and specifically provides a color filter that does not decrease luminance and thus is preferable for an image display device such as a liquid crystal display panel. Specifically, the present invention provides a novel compound represented by the following general formula (1), a dye using the compound, and a colored (alkali-developable) photosensitive composition and a color filter. The content of the above-mentioned general formula (1) is as described in the description.

10 Claims, No Drawings

COLORED PHOTOSENSITIVE COMPOSITION

TECHNICAL FIELD

The present invention relates to a dye that is designed to have a desired hue, and has improved heat-resistance, and a novel compound that is preferable for the dye. Furthermore, the present invention relates to a colored photosensitive composition using the dye, which is polymerizable by energy ray, and a color filter using the colored photosensitive composition.

BACKGROUND ART

Compounds having absorption with high intensity against specific light are used as optical elements of recording layers of optical recording media such as CD-Rs, DVD-Rs, DVD+Rs and BD-Rs, and of image display devices such as liquid crystal display devices (LCDs), plasma display panels (PDPs), electroluminescence displays (ELDs), cathode ray tube display devices (CRTs), fluorescent display tubes and field emission type displays.

In optical filters for image display devices such as liquid crystal display devices (LCDs), plasma display panels (PDPs), electroluminescence displays (ELDs), cathode ray tube display devices (CRTs), fluorescent display tubes and field emission type displays, various compounds that absorb light at wavelengths of 300 to 1,100 nm are used as light absorbing materials.

Furthermore, in recent years, light absorbing agents that selectively absorb wavelengths at specifically 380 to 500 nm are required so as to make the color purity and color separation of display elements sufficient to thereby improve image quality. For these light absorbing agents, especially steep light absorption, i.e., that the half width of λmax is small, and that the functions are not lost by light, heat and the like, are required.

Optical filters that are mainly used in liquid crystal display devices (LCDs) include color filters. Generally three primary colors of RGB have been used for color filters, but it is difficult to impart hues of pure RGB by a single color material, and thus efforts for making hues to those of pure RGB have been made by using plural color materials. Therefore, color materials of yellow, orange, purple and the like other than RGB are also required.

For light absorbing agents used for color filters, organic and/or inorganic pigments have been used due to their high heat-resistance, but the pigments have a problem that they decrease the luminance of display devices since they are pigments, and this problem has been solved by increasing the luminance of light sources. However, in accordance with the trend of low power consumption, dyes having excellent solubility in solvents and resin compositions and high heat-resistance, and color filters using the dyes have been actively developed. Patent Literatures 1 to 3 each discloses a dye using a compound having a specific structure. Patent Literature 4 discloses an optical filter using a compound having a specific structure.

However, the dyes (compounds) described in these documents are not satisfiable from the viewpoints of solubility and heat-resistance.

CITATION LIST

Patent Literature

Patent Literature 1: U.S. Pat. No. 4,925,782
Patent Literature 2: JP 03-053987 A
Patent Literature 3: JP 08-109335 A
Patent Literature 4: JP 2007-286189 A

SUMMARY OF INVENTION

Technical Problem

Accordingly, the present invention aims at providing a dye that is excellent in solubility and heat-resistance, and a novel compound that is suitable for the dye, and specifically aims at providing a yellow dye having the maximum absorption wavelength in the region of 420 to 470 nm. Furthermore, the present invention further aims at providing a colored (alkali-developable) photosensitive composition using the dye. In addition, the present invention further aims at providing an optical filter using the colored (alkali-developable) photosensitive composition, specifically a color filter that does not decrease luminance and thus is preferable for an image display device such as a liquid crystal display panel.

Solution to Problem

The present inventors did many intensive studies, and consequently found that a novel compound having a specific structure has the maximum absorption wavelength in the region of 420 to 470 nm, and that a dye using this compound is excellent in solubility and heat-resistance, and also found that a colored (alkali-developable) photosensitive composition using the above-mentioned dye does not decrease the luminance of an optical filter (specifically a color filter) and thus is preferable for a color filter for an image display device such as a liquid crystal display panel, and attained the present invention.

The present invention provides a novel compound represented by the following general formula (1).

[Chemical Formula 1]

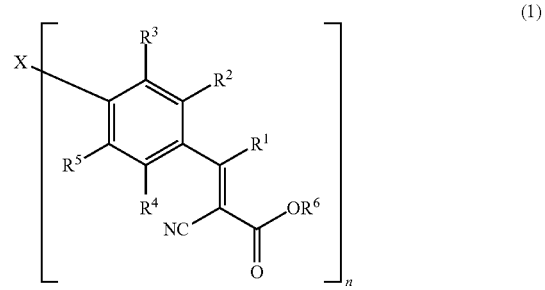

wherein
$R^1$ represents a hydrogen atom, a methyl group, a phenyl group or a cyano group,
$R^2$ to $R^5$ each independently represents a hydrogen atom, a halogen atom, a cyano group, a hydroxyl group, a nitro group, an alkyl group having 1 to 8 carbon atom(s), an alkoxy group having 1 to 8 carbon atom(s), a halogenated alkyl group having 1 to 8 carbon atom(s) or a halogenated alkoxy group having 1 to 8 carbon atom(s), wherein $R^2$ and $R^3$, and $R^4$ and $R^5$ may be respectively connected to each other to form a ring structure,
$R^6$ represents a hydrogen atom, an alkyl group having 1 to 8 carbon atom(s) or an aromatic hydrocarbongroup optionally having substituent(s) having 6 to 35 carbon atoms, wherein the alkyl group may be interrupted by —COO—, —O—, —OCO—, —NHCO—, —NH— or —CONH—, n represents an integer of 2 to 6, X represents a nitrogen atom, —$NR^{10}$—, an oxygen atom, a sulfur atom, —SO—, —$SO_2$—, a phosphorus atom, —$PR^{10}$—, or a substituent having 1 to 35 carbon atom(s) having a similar valency number to that of n, $R^{10}$ represents a hydrogen atom, an alkyl group having 1 to 8 carbon atom(s), an aryl group having 6 to 20 carbon atoms or an arylalkyl group having 7 to 20 carbon atoms, wherein the alkyl group, aryl group and arylalkyl group may be substituted with a halogen atom, a hydroxyl group, a nitro group or a cyano group, the alkyl group may be interrupted by —COO—, —O—, —OCO—, —NHCO—, —NH— or —CONH—, and $R^3$ and X, and $R^5$ and X may be respectively connected to each other to form a ring structure.

Furthermore, the present invention provides a dye containing at least one kind of the compound represented by the above-mentioned general formula (1) (hereinafter referred to as dye (A)).

Furthermore, the present invention provides a colored photosensitive composition containing the above-mentioned dye (A), (B) a polymerizable compound having an ethylenically unsaturated bond, and (C) a photopolymerization initiator, and further containing, as necessary, (D) an inorganic pigment and/or an organic pigment.

Furthermore, the present invention provides a colored photosensitive composition containing the above-mentioned dye (A), (B') a polymerizable compound having an ethylenically unsaturated bond, which has alkali-developability, and (C) a photopolymerization initiator, and further containing, as necessary, (D) an inorganic pigment and/or an organic pigment.

Furthermore, the present invention provides a cured product of the above-mentioned colored photosensitive composition or colored alkali-developable photosensitive composition, a color filter for a display device using the cured product, and a liquid crystal display panel using the color filter for a display device.

Advantageous Effect of Invention

According to the present invention, a dye that is excellent in solubility and heat-resistance, and a novel compound that is suitable for the dye can be provided. Furthermore, a colored photosensitive composition (colored alkali-developable photosensitive composition) using the dye and a cured product thereof are preferable for a color filter for a display device and a liquid crystal display panel.

DESCRIPTION OF EMBODIMENTS

Hereinafter the present invention will be explained in detail based on preferable exemplary embodiments.

First, the novel compound of the present invention will be explained. The novel compound of the present invention is represented by the above-mentioned general formula (1), and has a structure in which n specific groups are bound to a specific atom or group represented by X having a valency of n. These n groups may be the same or different from each other.

Examples of the halogen atom represented by $R^2$ to $R^5$ in the above-mentioned general formula (1) may include fluorine, chlorine, bromine and iodine, examples of the alkyl group having 1 to 8 carbon atom(s) may include methyl, ethyl, propyl, iso-propyl, butyl, sec-butyl, tert-butyl, iso-butyl, amyl, tert-amyl, hexyl, 2-hexyl, 3-hexyl, cyclohexyl, 4-methylcyclohexyl, heptyl, 2-heptyl, 3-heptyl, iso-heptyl, tert-heptyl, 1-octyl, iso-octyl, tert-octyl and the like, examples of the alkoxy group having 1 to 8 carbon atom(s) may include methyloxy, ethyloxy, iso-propyloxy, butyloxy, sec-butyloxy, tert-butyloxy, iso-butyloxy, amyloxy, iso-amyloxy, tert-amyloxy, hexyloxy, 2-hexyloxy, 3-hexyloxy, cyclohexyloxy, 4-methylcyclohexyloxy, heptyloxy, 2-heptyloxy, 3-heptyloxy, iso-heptyloxy, tert-heptyloxy, 1-octyloxy, iso-octyloxy, tert-octyloxy and the like, examples of the halogenated alkyl group having 1 to 8 carbon atom(s) may include chloromethyl, trifluoromethyl, dichloroethyl, nonafluoropropyl and the like, and examples of the halogenated alkoxy group having 1 to 8 carbon atom(s) may include chloromethyloxy, trifluoromethyloxy, dichloroethyloxy, nonafluoropropyloxy and the like.

Examples of the ring structure formed by the connection of $R^2$ and $R^3$ or $R^4$ and $R^5$ in the above-mentioned general formula (1) may include a cyclopentene ring, a cyclohexene ring, a dihydrofuran ring, a dihydropyran ring and the like.

Examples of the alkyl group having 1 to 8 carbon atom(s) represented by $R^6$ in the above-mentioned general formula (1) may include the groups exemplified in the explanation on the above-mentioned $R^2$ to $R^5$, and examples of the aromatic hydrocarbongroup optionally having substituent(s) having 6 to 35 carbon atoms may include benzyl, phenethyl, 2-phenylpropyl, diphenylmethyl, triphenylmethyl, 4-chlorophenylmethyl, benzyloxy, phenoxymethyl, phenoxyethyl, 1-naphthylmethoxy, 2-naphthylmethoxy, 1-anthrylmethoxy, benzylthio, phenylthiomethyl, phenylthioethyl, benzylsulfonyl, benzylcarbonyl, phenethylcarbonyl, 1-naphthylmethylcarbonyl, phenylacetate, 1-naphthylacetate, benzyloxycarbonyl, phenytyloxycarbonyl and the like.

Examples of the alkyl group having 1 to 8 carbon atom(s) represented by $R^{10}$ that is a group in X in the above-mentioned general formula (1) may include the groups that are exemplified in the explanation on $R^2$ in the above-mentioned general formula (1), examples of the aryl group having 6 to 20 carbon atoms may include phenyl, naphthyl, 2-methylphenyl, 3-methylphenyl, 4-methylphenyl, 4-vinylphenyl, 3-iso-propylphenyl, 4-iso-propylphenyl, 4-butylphenyl, 4-iso-butylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,4,5-trimethylphenyl and the like, and examples of the arylalkyl group having 7 to 20 carbon atoms may include benzyl, phenethyl, 2-phenylpropan-2-yl, diphenylmethyl, triphenylmethyl, styryl, cinnamyl and the like.

Examples of the substituent having 1 to 35 carbon atom(s) having the same valency number as n, which is represented by X in the above-mentioned general formula (1), may include an aliphatic hydrocarbongroup having 1 to 35 carbon atom(s) optionally having substituents, an aromatic hydrocarbongroup substituent optionally having substituents and a heterocyclic group optionally having substituents, and the like.

Examples of the substituents that may be possessed by the aliphatic hydrocarbongroup, aromatic hydrocarbongroup and heterocyclic group having 1 to 35 carbon atom(s) represented by X in the above-mentioned general formula (1) may include alkyl groups such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl and decyl;

alkoxy groups such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy and decyloxy;

alkylthio groups such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio and 2-ethylhexylthio;

alkenyl groups such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl and tricosenyl;

arylalkyl groups such as benzyl, phenethyl, diphenylmethyl, triphenylmethyl, styryl and cinnamyl;

aryl groups such as phenyl and naphthyl;

aryloxy groups such as phenoxy and naphthyloxy;

arylthio groups such as phenylthio and naphthylthio;

heterocyclic groups such as pyridyl, pyrimidyl, pyridazyl, piperidyl, pyranyl, pyrazolyl, triazyl, pyrrolyl, quinolyl, isoquinolyl, imidazolyl, benzoimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl and 2,4-dioxyoxazolidin-3-yl;

halogen atoms such as fluorine, chlorine, bromine and iodine;

acyl groups such as acetyl, 2-chloroacetyl, propionyl, octanoyl, acryloyl, methacryloyl, phenylcarbonyl(benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl and carbamoyl;

acyloxy groups such as acetyloxy and benzoyloxy;

substituted amino groups such as amino, ethylamino, dimethylamino, diethylamino, butylamino, cyclopentylamino, 2-ethylhexylamino, dodecylamino, anilino, chlorophenylamino, toluidino, anisidino, N-methyl-anilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino and phenylsulfonylamino;

a sulfonamide group, a sulfonyl group, a carboxyl group, a cyano group, a sulfo group, a hydroxyl group, a nitro group, a mercapto group, an imide group, a carbamoyl group, a sulfonamide group and the like, and these groups may further be substituted.

Furthermore, the carboxyl group and sulfo group may form salts.

The chain hydrocarbons in these substituents may optionally be interrupted by —COO—, —O—, —OCO—, —NHCO—, —NH— or —CONH—.

Specific examples of the group represented by X in the above-mentioned general formula (1) may include the group represented by the following general formula (2) when n is 2, the group represented by the following general formula (3) when n is 3, the group represented by the following general formula (4) when n is 4, the group represented by the following general formula (5) when n is 5, and the group represented by the following general formula (6) when n is 6.

[Chemical Formula 2]

$$*-Z^1-X^1-Z^1-* \qquad (2)$$

wherein in the above-mentioned general formula (2), $X^1$ represents —$CR^{20}R^{21}$—, —$NR^{20}$—, a chain hydrocarbon having 1 to 30 carbon atom(s), an alicyclic hydrocarbon having 3 to 30 carbon atoms, an aromatic hydrocarbon having 6 to 30 carbon atoms or a heterocycle having 6 to 30 carbon atoms, which is di-substituted, or any of the substituents represented by the following [Chemical Formula 3] to [Chemical Formula 5], wherein the chain hydrocarbon may be interrupted by —COO—, —O—, —OCO—, —NHCO—, —NH— or —CONH—, $R^{20}$ and $R^{21}$ each represents a hydrogen atom, an alkyl group having 1 to 8 carbon atom(s), an aryl group having 6 to 20 carbon atoms or an arylalkyl group having 7 to 20 carbon atoms, and $Z^1$ and $Z^2$ each represents a direct bond, —O—, —S—, —$SO_2$—, —SS—, —SO—, —$NR^{10}$— or —$PR^{10}$—, wherein $R^{10}$ is as defined in the above-mentioned general formula (1), provided that the total of the number of the carbon atoms in the group represented by the above-mentioned general formula (2) is within the range of 1 to 35.

[Chemical Formula 3]

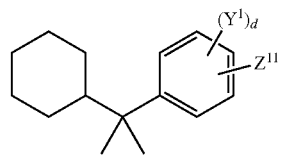

wherein in the above-mentioned formula, $Z^{11}$ represents a hydrogen atom, a phenyl group optionally substituted by an alkyl group or alkoxy group having 1 to 10 carbon atom(s), or a cycloalkyl group having 3 to 10 carbon atoms, $Y^1$ represents an alkyl group having 1 to 10 carbon atom(s), an alkoxy group having 1 to 10 carbon atom(s), an alkenyl group having 2 to 10 carbon atoms or a halogen atom, wherein the above-mentioned alkyl group, alkoxy group and alkenyl group may be substituted with halogen atom(s), and d is an integer of 0 to 5.

[Chemical Formula 4]

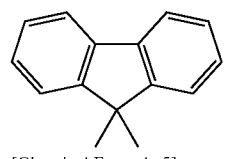

[Chemical Formula 5]

-continued

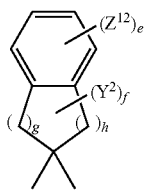

wherein in the above-mentioned formula, $Y^2$ and $Z^{12}$ each independently represents an alkyl group having 1 to 10 carbon atom(s) optionally substituted with halogen atom(s), an aryl group having 6 to 20 carbon atoms optionally substituted with halogen atom(s), an aryloxy group having 6 to 20 carbon atoms optionally substituted with halogen atom(s), an arylthio group having 6 to 20 carbon atoms optionally substituted with halogen atom(s), an arylalkenyl group having 6 to 20 carbon atoms optionally substituted with halogen atom(s), an arylalkyl group having 7 to 20 carbon atoms optionally substituted with halogen atom(s), a heterocyclic group having 2 to 20 carbon atoms optionally substituted with halogen atom(s), or a halogen atom, wherein the methylene group(s) in the alkyl group and arylalkyl group may be interrupted with an unsaturated bond, —O— or —S—, $Z^{12}$ may form a ring with the adjacent $Z^{12}$, e represents a number of 0 to 4, f represents a number of 0 to 8, g represents a number of 0 to 4, h represents a number of 0 to 4, and the total of the numbers of g and h is 2 to 4.

[Chemical Formula 6]

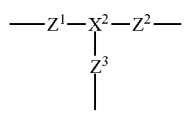

(3)

wherein in the above-mentioned general formula (3), $X^2$ represents a carbon atom substituted with $R^{30}$, or a chain hydrocarbon having 1 to 30 carbon atom(s), an alicyclic hydrocarbon having 3 to 30 carbon atoms, an aromatic hydrocarbon having 6 to 30 carbon atoms or a heterocycle having 6 to 30 carbon atoms, which is tri-substituted, $R^{30}$ represents a hydrogen atom, an alkyl group having 1 to 8 carbon atom(s), an aryl group having 6 to 25 carbon atoms or an arylalkyl group having 7 to 25 carbon atoms, wherein the chain hydrocarbon may be interrupted by —COO—, —O—, —OCO—, —NHCO—, —NH— or —CONH—, and $Z^1$ to $Z^3$ are each the same as the group represented by $Z^1$ in the above-mentioned general formula (2), provided that the total of the number of the carbon atoms in the group represented by the above-mentioned general formula (3) is within the range of 1 to 35.

[Chemical Formula 7]

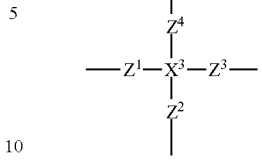

(4)

wherein in the above-mentioned general formula (4), $X^3$ represents a carbon atom, or a chain hydrocarbon having 1 to 30 carbon atom(s), an alicyclic hydrocarbon having 3 to 30 carbon atoms, an aromatic hydrocarbon having 6 to 30 carbon atoms or a heterocycle having 6 to 30 carbon atoms, which is tetra-substituted, wherein the chain hydrocarbon may be interrupted by —COO—, —O—, —OCO—, —NHCO—, —NH— or —CONH—, and $Z^1$ to $Z^4$ are each the same as the group represented by $Z^1$ in the above-mentioned general formula (2), provided that the total of the number of the carbon atoms in the group represented by the above-mentioned general formula (4) is within the range of 1 to 35.

[Chemical Formula 8]

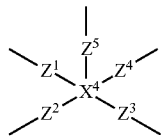

(5)

wherein in the above-mentioned general formula (5), $X^4$ is a chain hydrocarbon having 1 to 30 carbon atom(s), an alicyclic hydrocarbon having 3 to 30 carbon atoms, an aromatic hydrocarbon having 6 to 30 carbon atoms or a heterocycle having 6 to 30 carbon atoms, which is penta-substituted, wherein the chain hydrocarbon may be interrupted by —COO—, —O—, —OCO—, —NHCO—, —NH— or —CONH—, and $Z^1$ to $Z^5$ are each the same as the group represented by $Z^1$ in the above-mentioned general formula (2), provided that the total of the number of the carbon atoms in the group represented by the above-mentioned general formula (5) is within the range of 1 to 35.

[Chemical Formula 9]

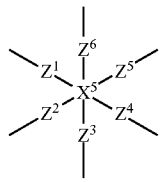

(6)

wherein in the above-mentioned general formula (6), $X^5$ is a chain hydrocarbon having 1 to 30 carbon atom(s), an alicyclic hydrocarbon having 3 to 30 carbon atoms, an aromatic hydrocarbon having 6 to 30 carbon atoms or a heterocycle having 6 to 30 carbon atoms, which is hexa-substituted, wherein the chain hydrocarbon may be interrupted by —COO—, —O—, —OCO—, —NHCO—, —NH— or —CONH—, and $Z^1$ to $Z^6$ are each the same as the group represented by $Z^1$ in the above-mentioned general formula (2), provided that the total of the number of the carbon atoms in the group represented by the above-mentioned general formula (6) is within the range of 1 to 35.

Examples of the di-substituted chain hydrocarbon having 1 to 30 carbon atom(s) represented by $X^1$ in the above-mentioned general formula (2) may include groups formed by substituting methane, ethane, propane, iso-propane, butane, sec-butane, tert-butane, iso-butane, hexane, 2-methylhexane, 3-methylhexane, heptane, 2-methylheptane, 3-methylheptane, iso-heptane, tert-heptane, 1-methyloctane, iso-octane, tert-octane and the like with $Z^1$ and $Z^2$ (di-substituted), examples of the di-substituted alicyclic hydrocarbons having 3 to 30 carbon atoms may include groups formed by substituting cyclopropane, cyclobutane, cyclopentane, cyclohexane, cycloheptane, 2,4-dimethylcyclobutane, 4-methylcyclohexane and the like with $Z^1$ and $Z^2$ (di-substituted), and the like, examples of the di-substituted aromatic hydrocarbons having 6 to 30 carbon atoms may include groups formed by substituting groups such as phenylene, naphthylene and biphenyl with $Z^1$ and $Z^2$ (di-substituted), and the like, and examples of the di-substituted heterocycle having 6 to 30 carbon atoms may include groups formed by substituting pyridine, pyrazine, piperidine, piperazine, pyrimidine, pyridazine, triazine, hexahydrotriazine, furan, tetrahydrofuran, chromane, xanthene, thiophene, thiolane and the like with $Z^1$ and $Z^2$ (di-substituted).

These groups may further by substituted by a halogen atom, a cyano group, a nitro group or an alkoxy group having 1 to 8 carbon atom(s) represented by the above-mentioned $R^2$.

The alkyl group having 1 to 8 carbon atom(s), aryl group having 6 to 20 carbon atoms and arylalkyl group having 7 to 20 carbon atoms represented by $R^{20}$ and $R^{21}$ that are groups in $X^1$ in the above-mentioned general formula (2) may include the groups exemplified in the explanation on $R^{10}$ that is the group in X in the above-mentioned general formula (1).

The tri-substituted chain hydrocarbon having 1 to 30 carbon atom(s) that is represented by $X^2$ in the above-mentioned general formula (3) may include groups formed by substituting the chain hydrocarbons as exemplified in the explanation on $X^1$ in the above-mentioned general formula (2) with $Z^1$, $Z^2$ and $Z^3$ (tri-substituted), examples of the tri-substituted alicyclic hydrocarbon having 3 to 30 carbon atoms may include groups formed by substituting the alicyclic hydrocarbons as exemplified in the explanation on $X^1$ in the above-mentioned general formula (2) with $Z^1$, $Z^2$ and $Z^3$ (tri-substituted), examples of the tri-substituted aromatic hydrocarbon having 6 to 30 carbon atoms may include groups formed by substituting the aromatic hydrocarbons as exemplified in the explanation on $X^1$ in the above-mentioned general formula (2) with $Z^1$, $Z^2$ and $Z^3$ (tri-substituted), and examples of the tri-substituted heterocycle having 6 to 30 carbon atoms may include groups formed by substituting the heterocycles as exemplified in the explanation on $X^1$ in the above-mentioned general formula (2) with $Z^1$, $Z^2$ and $Z^3$ (tri-substituted).

Examples of the alkyl group having 1 to 8 carbon atom(s), aryl group having 6 to 25 carbon atoms or arylalkyl group having 7 to 25 carbon atoms represented by $R^{30}$ that is the group in $X^2$ in the above-mentioned general formula (3) may include the groups as exemplified in the explanation on $R^{20}$ in the above-mentioned general formula (2), and the like.

Examples of the tetra-substituted chain hydrocarbon having 1 to 30 carbon atom(s) represented by $X^3$ in the above-mentioned general formula (4) may include groups formed by substituting the chain hydrocarbons as exemplified in the explanation on $X^1$ in the above-mentioned general formula (2) with $Z^1$, $Z^2$, $Z^3$ and $Z^4$ (tetra-substituted), examples of the tetra-substituted alicyclic hydrocarbon having 3 to 30 carbon atoms may include groups formed by substituting the alicyclic hydrocarbons as exemplified in the explanation on $X^1$ in the above-mentioned general formula (2)

with $Z^1$, $Z^2$, $Z^3$ and $Z^4$ (tetra-substituted), examples of the tetra-substituted aromatic hydrocarbon having 6 to 30 carbon atoms may include groups formed by substituting the aromatic hydrocarbons as exemplified in the explanation on $X^1$ in the above-mentioned general formula (2) with $Z^1$, $Z^2$, $Z^3$ and $Z^4$ (tetra-substituted), and examples of the tetra-substituted heterocycle having 6 to 30 carbon atoms may include groups formed by substituting the heterocycles as exemplified in the explanation on $X^1$ in the above-mentioned general formula (2) with $Z^1$, $Z^2$, $Z^3$ and $Z^4$ (tetra-substituted).

Examples of the penta-substituted chain hydrocarbon having 1 to 30 carbon atom(s) represented by $X^4$ in the above-mentioned general formula (5) may include groups formed by substituting the chain hydrocarbons as exemplified in the explanation on $X^1$ in the above-mentioned general formula (2) with $Z^1$, $Z^2$, $Z^3$, $Z^4$ and $Z^5$ (penta-substituted), examples of the penta-substituted alicyclic hydrocarbon having 3 to 30 carbon atoms may include groups formed by substituting the alicyclic hydrocarbons as exemplified in the explanation on $X^1$ in the above-mentioned general formula (2) with $Z^1$, $Z^2$, $Z^3$, $Z^4$ and $Z^5$ (penta-substituted), examples of the penta-substituted aromatic hydrocarbon having 6 to 30 carbon atoms may include groups formed by substituting the aromatic hydrocarbons as exemplified in the explanation on $X^1$ in the above-mentioned general formula (2) with $Z^1$, $Z^2$, $Z^3$, $Z^4$ and $Z^5$ (penta-substituted), and examples of the penta-substituted heterocycle having 6 to 30 carbon atoms may include groups formed by substituting the heterocycles as exemplified in the explanation on $X^1$ in the above-mentioned general formula (2) with $Z^1$, $Z^2$, $Z^3$, $Z^4$ and $Z^5$ (penta-substituted).

Examples of the hexa-substituted chain hydrocarbon having 1 to 30 carbon atom(s) represented by $X^5$ in the above-mentioned general formula (6) may include groups formed by substituting the chain hydrocarbons as exemplified in the explanation on $X^1$ in the above-mentioned general formula (2) with $Z^1$, $Z^2$, $Z^3$, $Z^4$, $Z^5$ and $Z^6$ (hexa-substituted), examples of the hexa-substituted alicyclic hydrocarbon having 3 to 30 carbon atoms may include groups formed by substituting the alicyclic hydrocarbons as exemplified in the explanation on $X^1$ in the above-mentioned general formula (2) with $Z^1$, $Z^2$, $Z^3$, $Z^4$, $Z^5$ and $Z^6$ (hexa-substituted), examples of the hexa-substituted aromatic hydrocarbon having 6 to 30 carbon atoms may include groups formed by substituting the aromatic hydrocarbons as exemplified in the explanation on $X^1$ in the above-mentioned general formula (2) with $Z^1$, $Z^2$, $Z^3$, $Z^4$, $Z^5$ and $Z^6$ (hexa-substituted), and examples of the hexa-substituted heterocycle having 6 to 30 carbon atoms may include groups formed by substituting the heterocycles as exemplified in the explanation on $X^1$ in the above-mentioned general formula (2) with $Z^1$, $Z^2$, $Z^3$, $Z^4$, $Z^5$ and $Z^6$ (hexa-substituted).

Among the compounds represented by the above-mentioned general formula (1), the compounds wherein $R^1$ is a hydrogen atom; the compounds wherein $R^2$ to $R^5$ are each a hydrogen atom; the compounds wherein $R^6$ is an alkyl group having 1 to 4 carbon atoms; the compounds wherein, when n is 2, X is a group selected from Group 1; the compounds wherein, when n is 3, X is a group selected from Group 2; the compounds wherein, when n is 4, X is a group selected from Group 3; the compounds wherein, when n is 5, X is a group selected from Group 4; and the compounds wherein, when n is 6, X is a group selected from Group 5 are preferable since obtainment of raw materials and production are easy.

Furthermore, among the compounds represented by the above-mentioned general formula (1), the compounds wherein n is 3 or more are preferable since they are excellent in heat-resistance.

[Chemical Formula 10]

<Group 1>

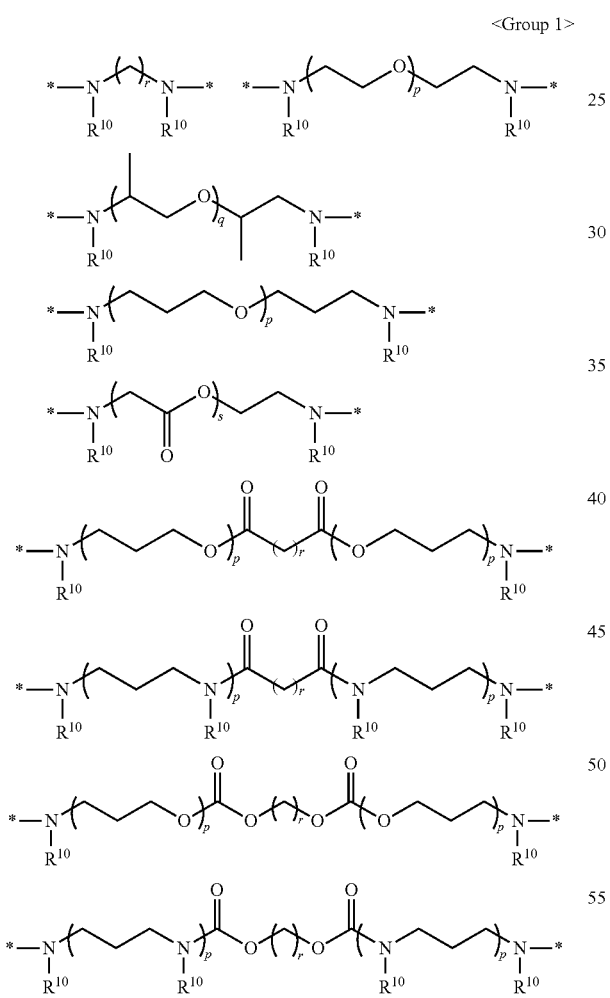

[Chemical Formula 11]

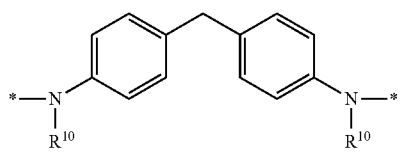

-continued

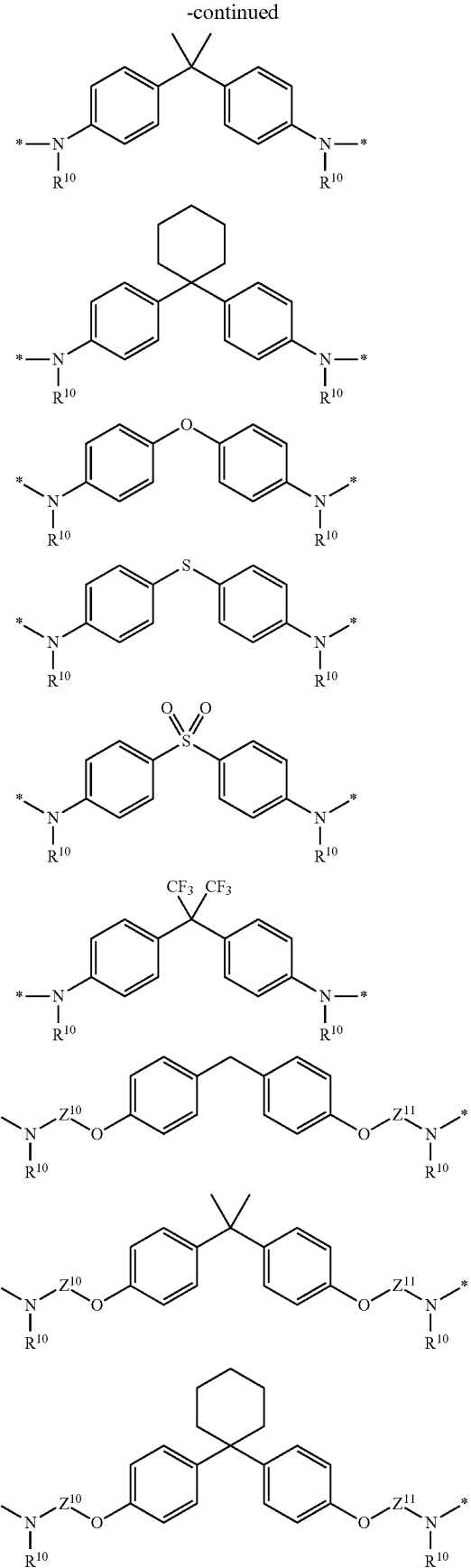

-continued
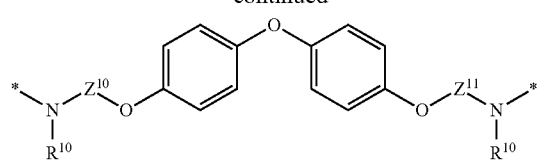
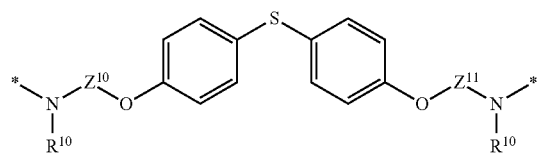
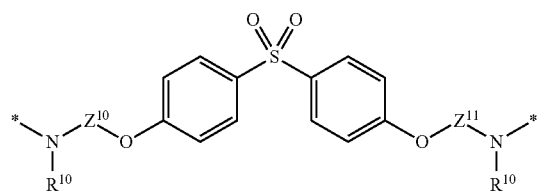
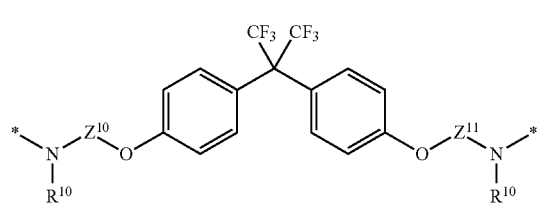
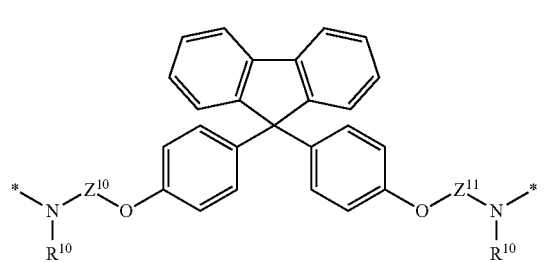
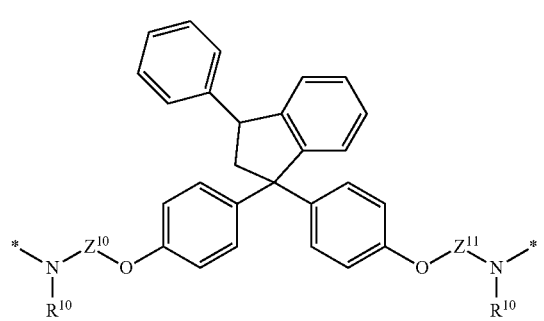
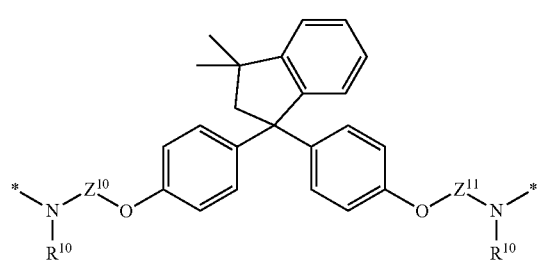
-continued
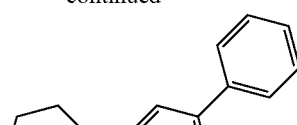
[Chemcial Formula 12]
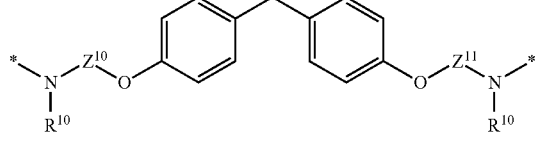
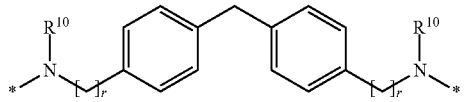
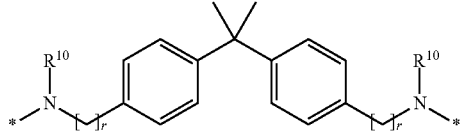
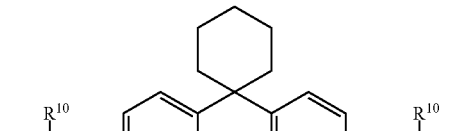
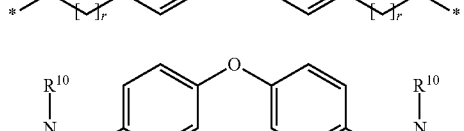
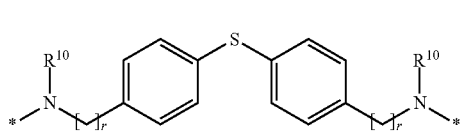
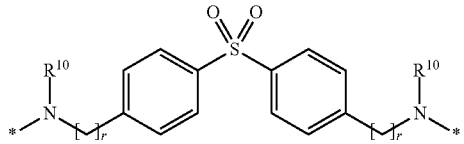
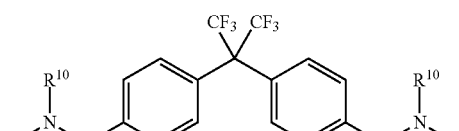
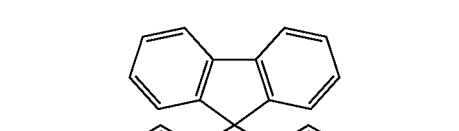

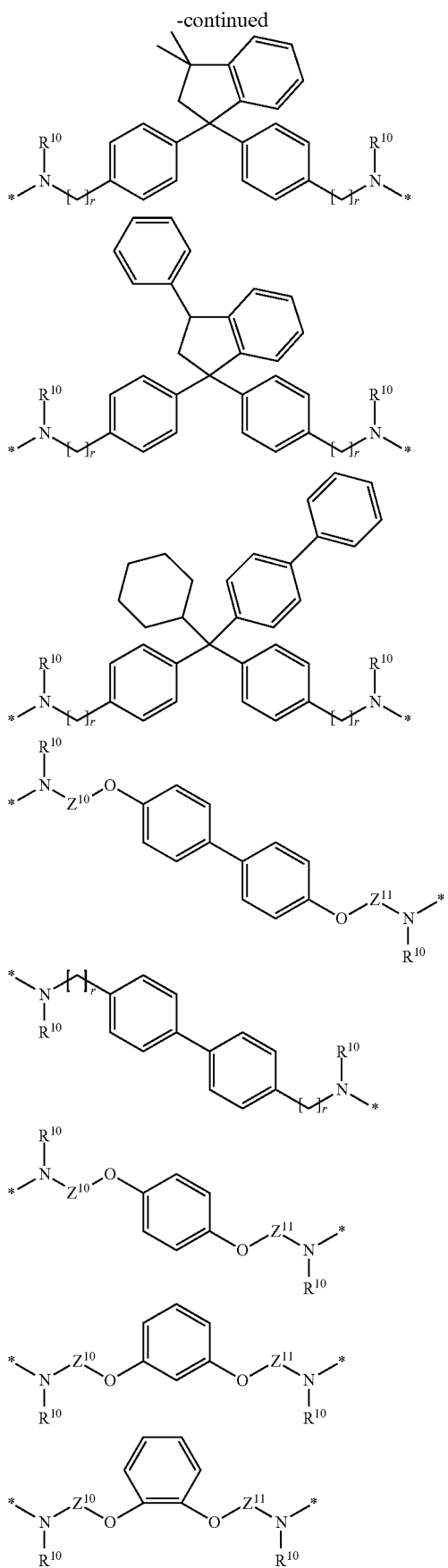

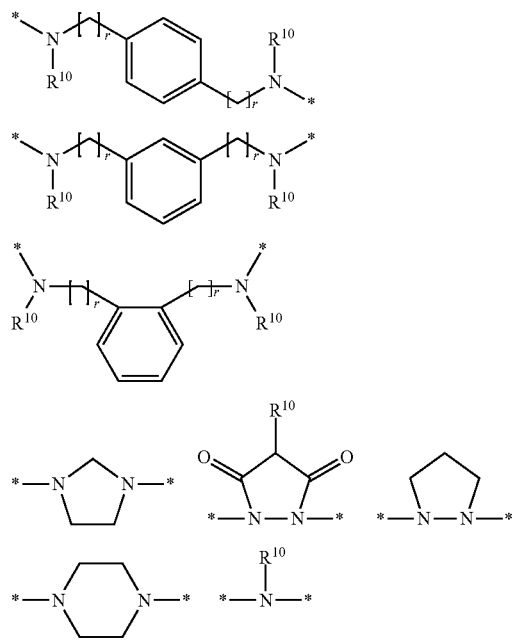

wherein in the above-mentioned formulas, $R^{10}$ is the same group as $R^{10}$ in the above-mentioned general formula (2), and in the case when two or more $R^{10}$s are present in the group, $R^{10}$s may be the same or different, $Z^{10}$ and $Z^{11}$ each represents a bivalent group selected from the following Group A, p represents an integer of 1 to 3, q represents an integer of 0 to 3, r represents an integer of 1 to 19, and s represents an integer of 1 to 3.

[Chemical Formula 13]

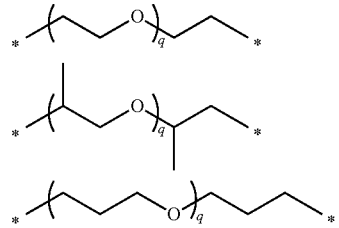

<Group A> wherein in the above-mentioned formulas, q represents an integer of 0 to 3.

[Chemical Formula 14]

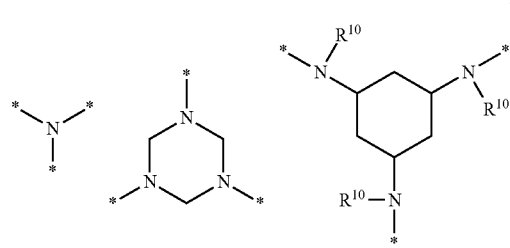

<Group2>

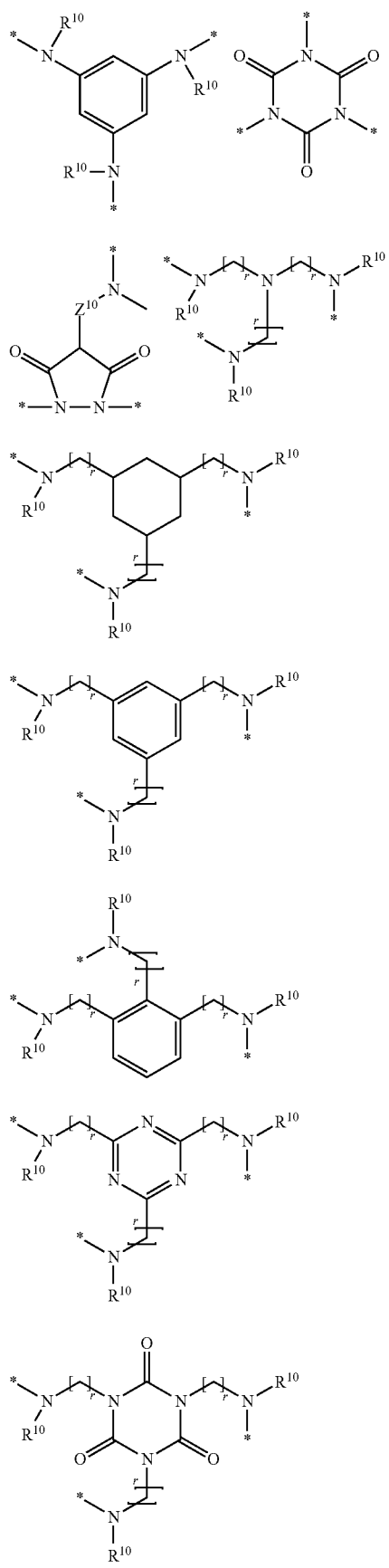
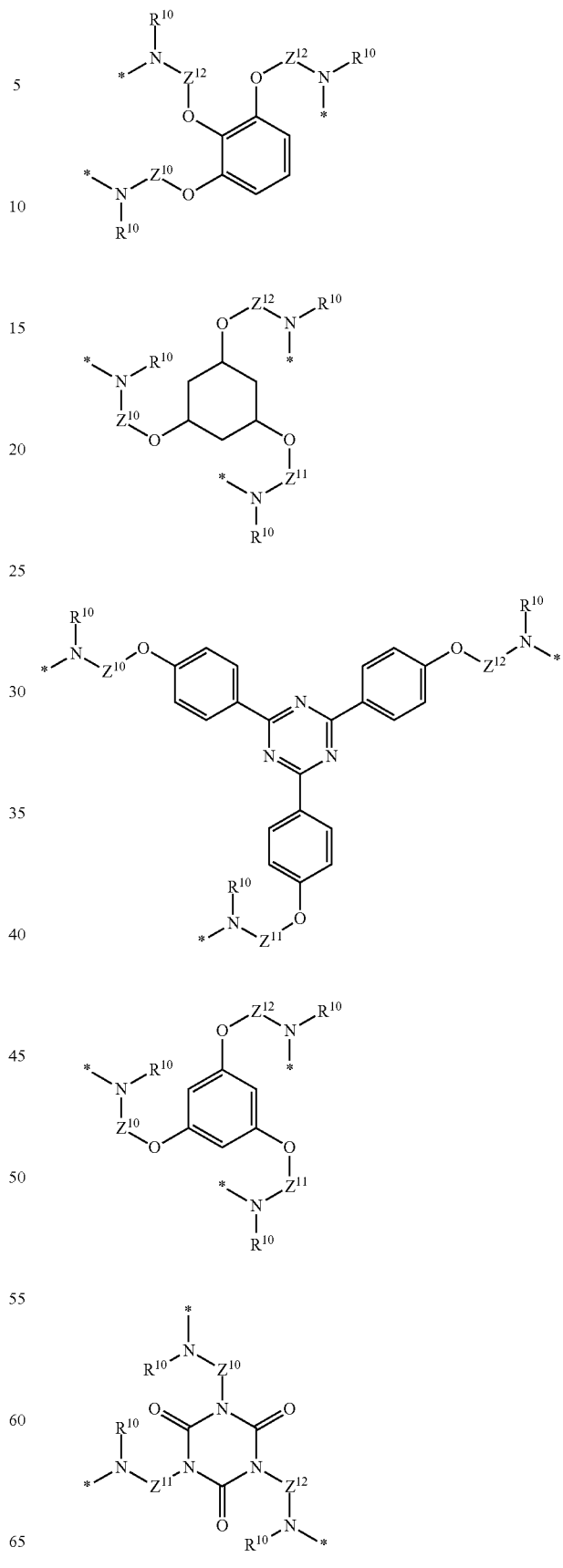

wherein in the above-mentioned formulas, $R^{10}$ is the same group as $R^{10}$ in the above-mentioned general formula (2), and in the case when two or more $R^{10}$s are present in the group, $R^{10}$s may be the same or different, $Z^{10}$, $Z^{11}$ and $Z^{12}$ each represents a bivalent group selected from the above-mentioned Group A, and r represents an integer of 1 to 19.

[Chemical Formula 15]

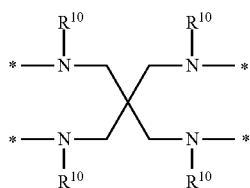

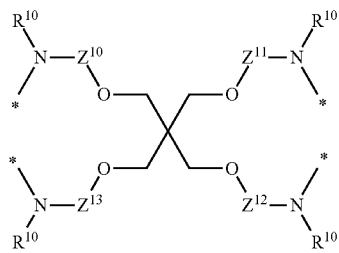

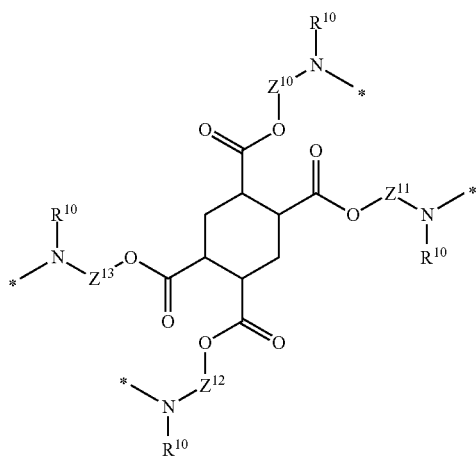

wherein in the above-mentioned formulas, $R^{10}$ is the same group as $R^{10}$ in the above-mentioned general formula (2), and in the case when two or more $R^{10}$s are present in the group, RN may be the same or different, and $Z^{10}$, $Z^{11}$, $Z^{12}$ and $Z^{13}$ each represents a bivalent group selected from the above-mentioned Group A.

[Chemical Formula 16]

<Group 3>

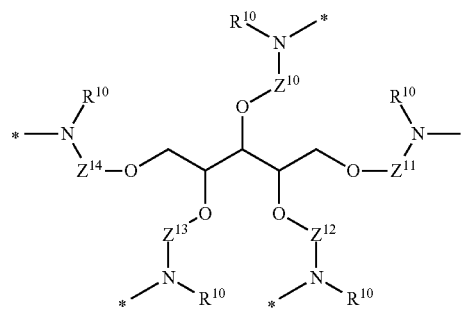

<Group 4>

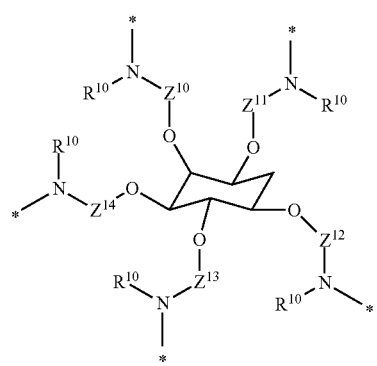

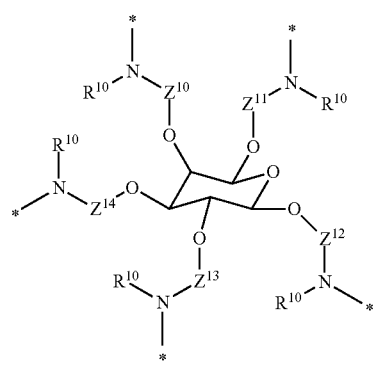

wherein in the above-mentioned formulas, $R^{10}$ is the same group as $R^{10}$ in the above-mentioned general formula (2), and in the case when two or more $R^{10}$s are present in the group, RN may be the same or different, and $Z^{10}$, $Z^{11}$, $Z^{12}$, $Z^{13}$ and $Z^{14}$ each represents a bivalent group selected from the above-mentioned Group A.

[Chemical Formula 17]

<Group 5>

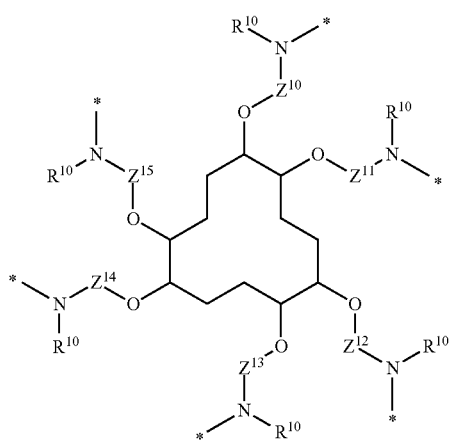

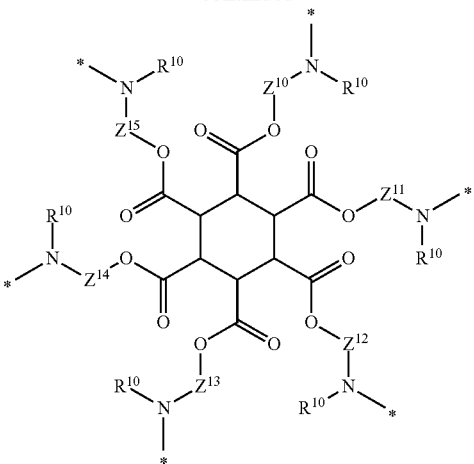

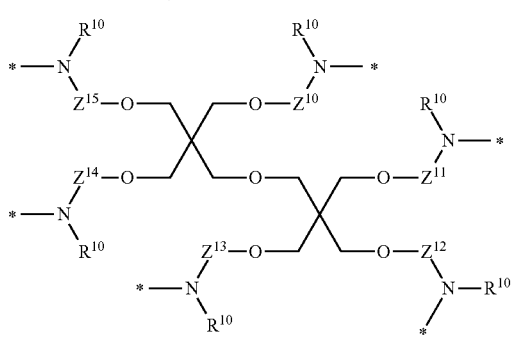

wherein in the above-mentioned formulas, $R^{10}$ is the same group as $R^{10}$ in the above-mentioned general formula (2), and in the case when two or more RN are present in the group, $R^{10}$s may be the same or different, and $Z^{10}$, $Z^{11}$, $Z^{12}$, $Z^{13}$, $Z^{14}$ and $Z^{15}$ each represents a bivalent group selected from the above-mentioned Group A.

Specific examples of the compound represented by the above-mentioned general formula (1) may include the following compounds No. 1 to No. 89, but the present invention is not limited by these compounds.

[Chemical Formula 18]

Compound No. 1

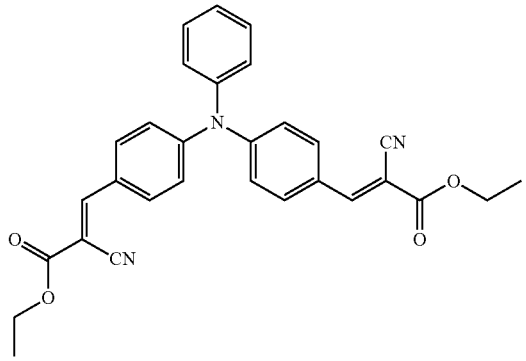

Compound No. 2

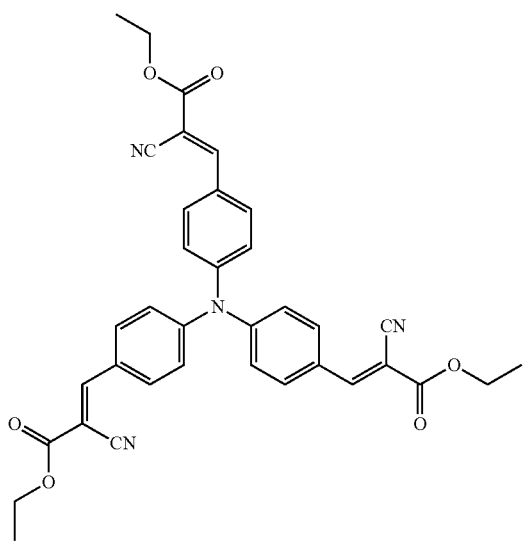

-continued
Compound No. 3
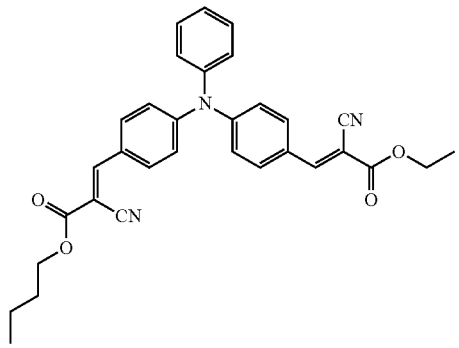
Compound No. 4
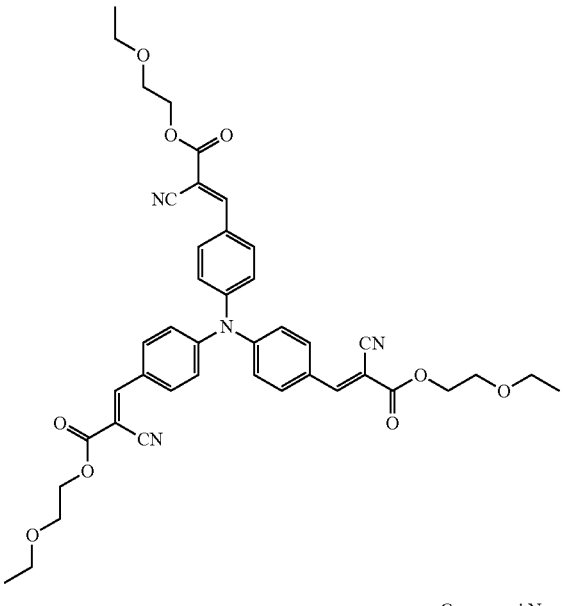
Compound No. 5
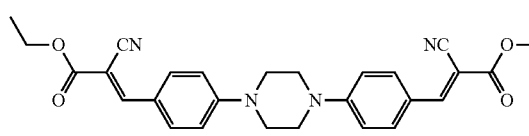
Compound No. 6
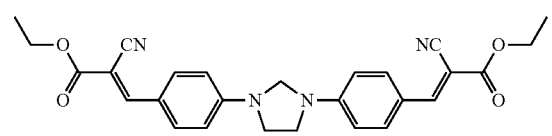
Compound No. 7
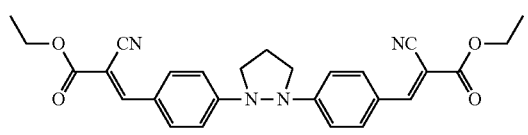
Compound No. 8
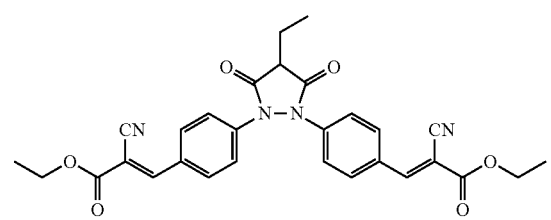
[Chemical Formula 19]
Compound No. 9
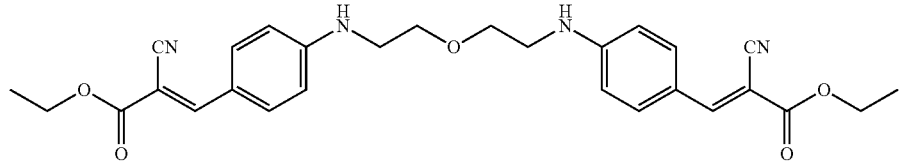
Compound No. 10
Compound No. 11
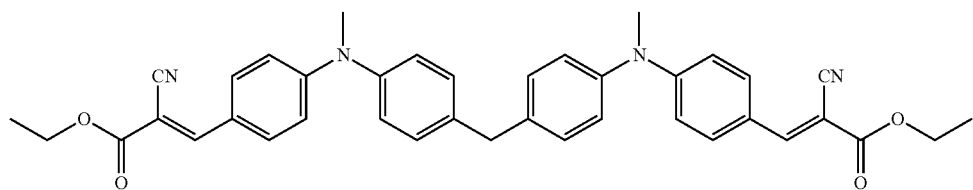

Compound No. 12
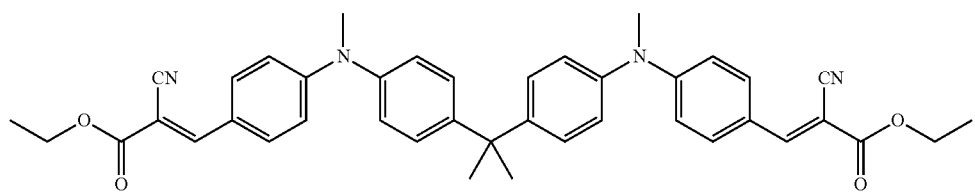
Compound No. 13
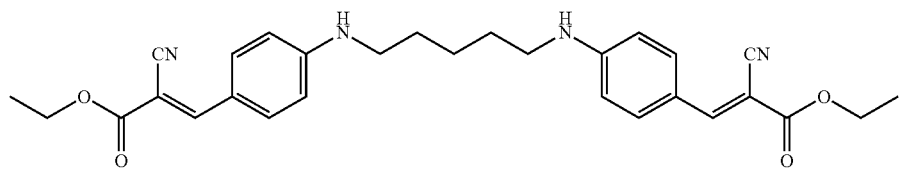
[Chemical Formula 20]
Compound No. 14
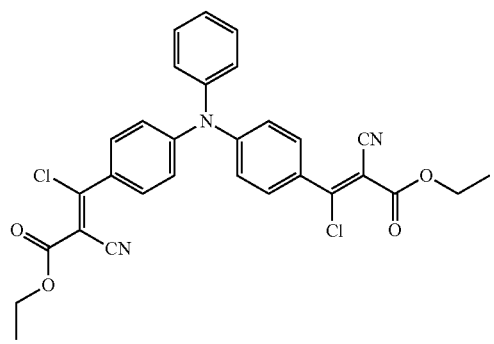
Compound No. 15
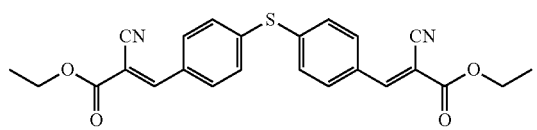
Compound No. 16
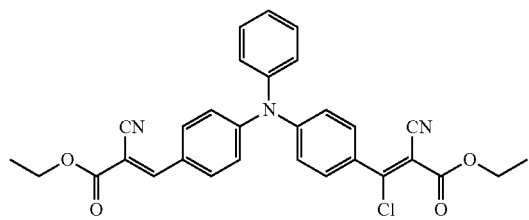
Compound No. 17
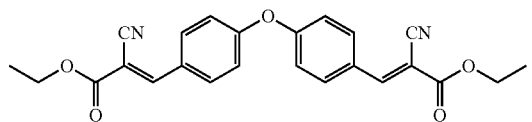
Compound No. 18
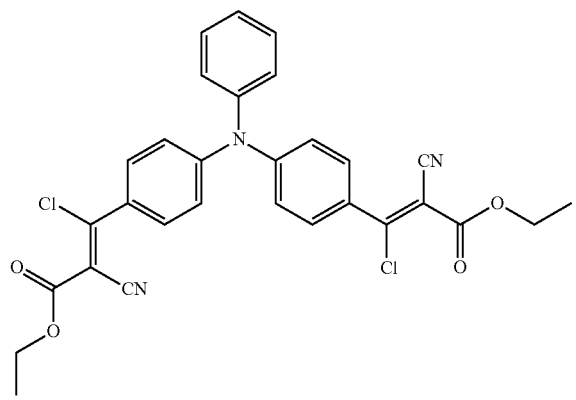

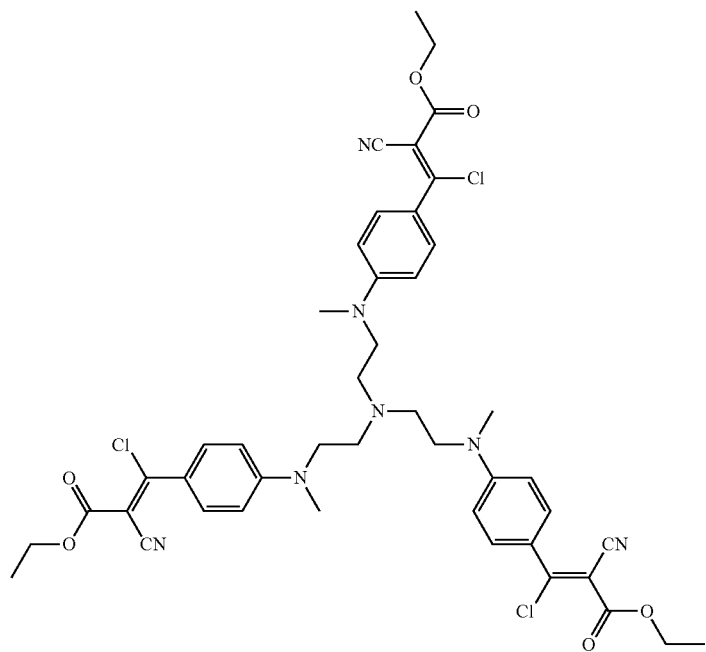
Compound No. 19
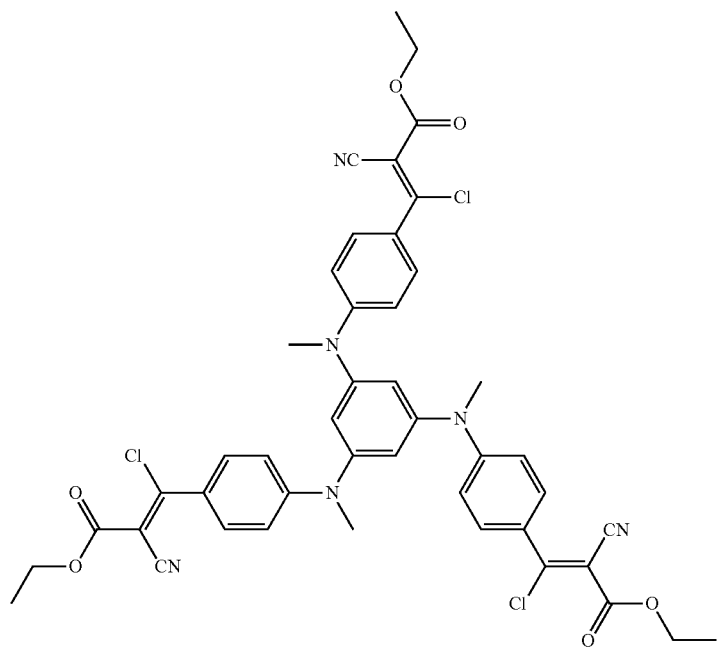
Compound No. 20

[Chemical Formula 21]
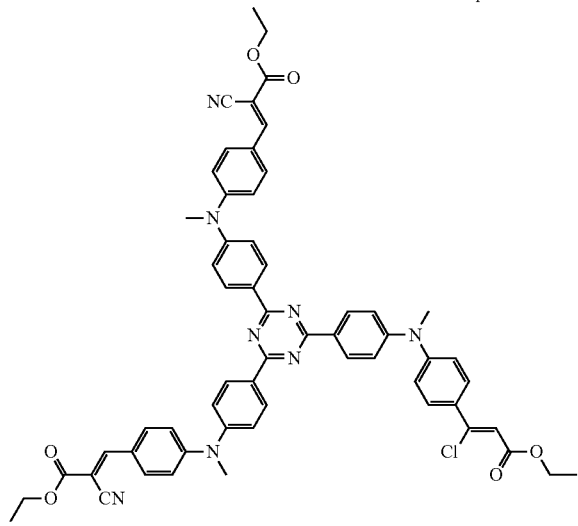
Compound No. 21
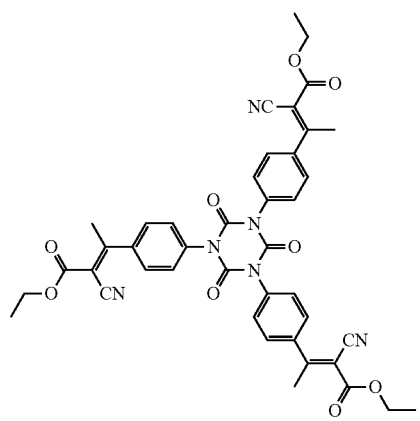
Compound No. 22
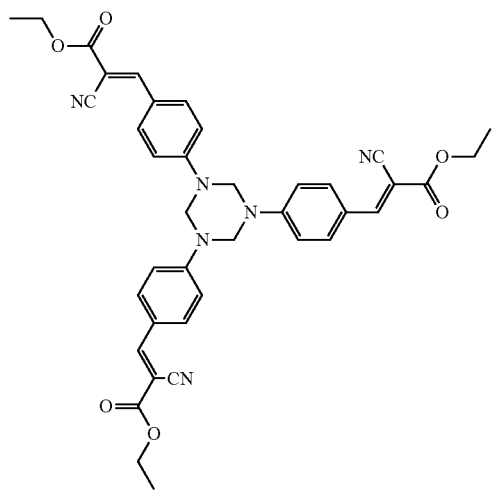
Compound No. 23
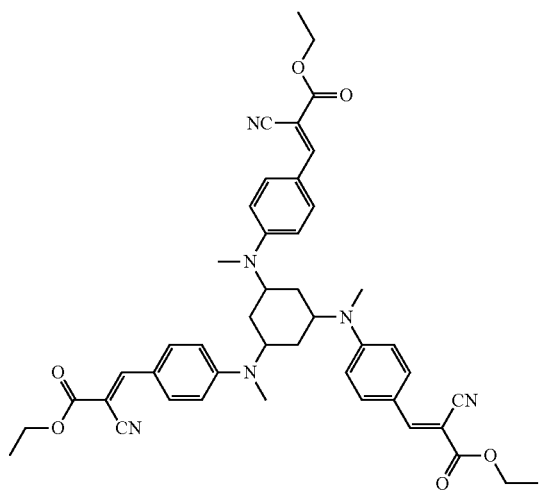
Compound No. 24

[Chemical Formula 22]
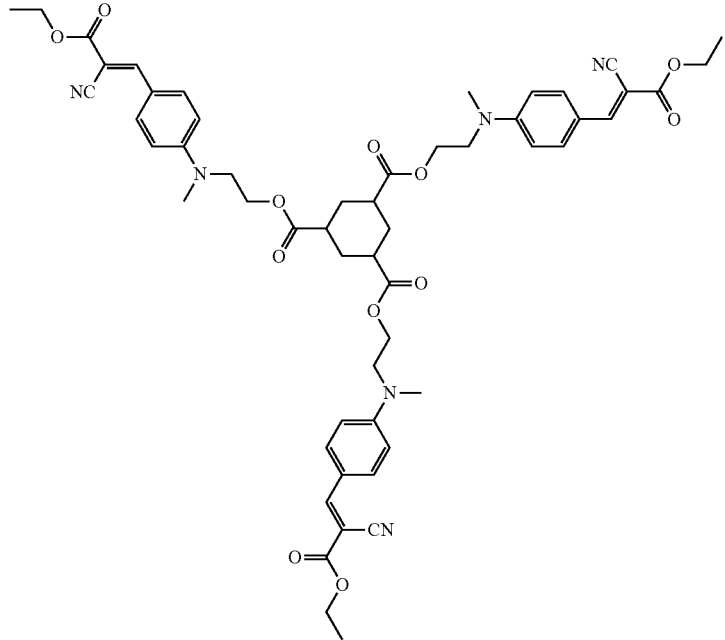
Compound No. 25
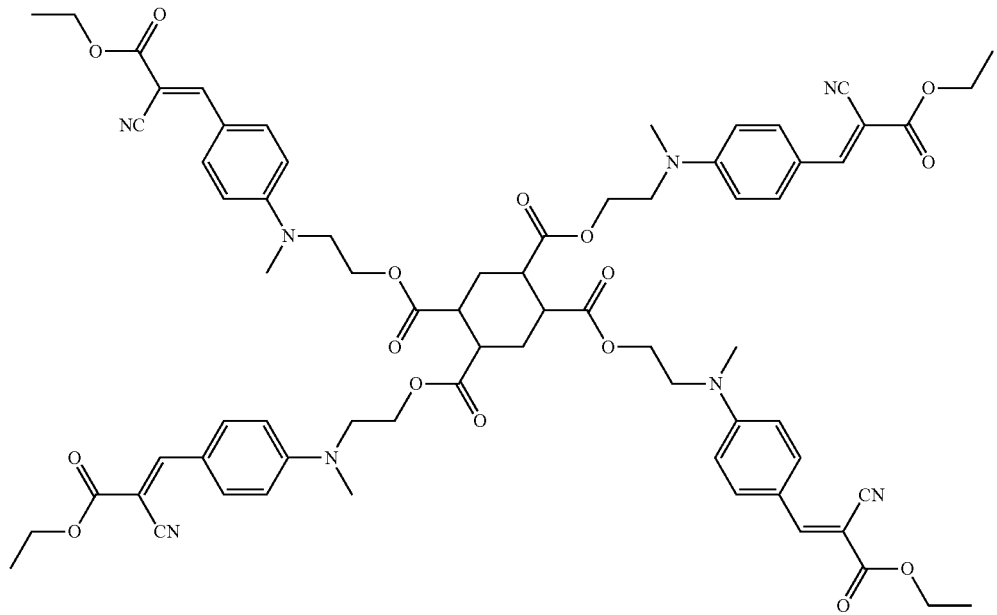
Compound No. 26

[Chemical Formula 23]
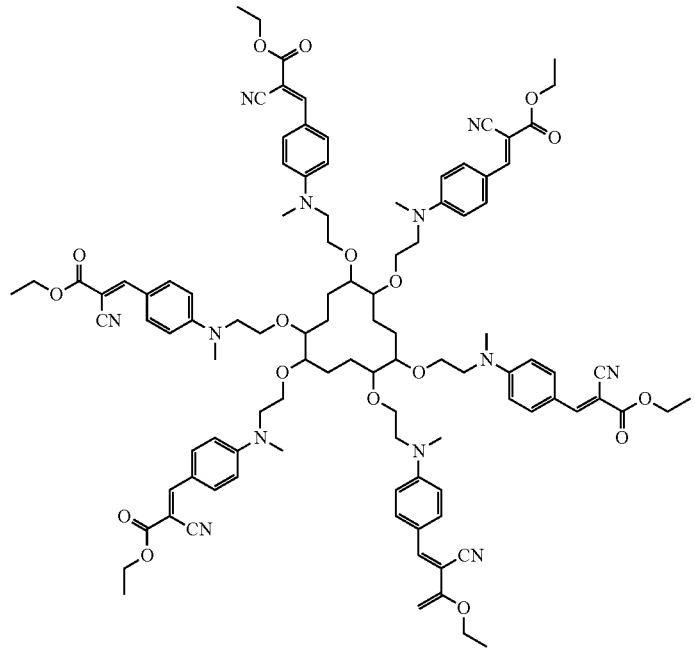
Compound No. 27
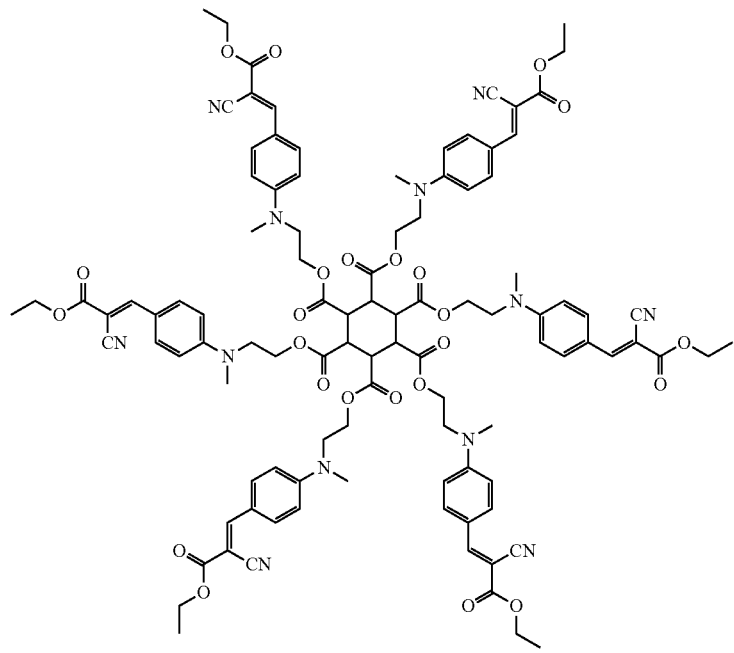
Compound No. 28

[Chemical Formula 24]
Compound No. 29
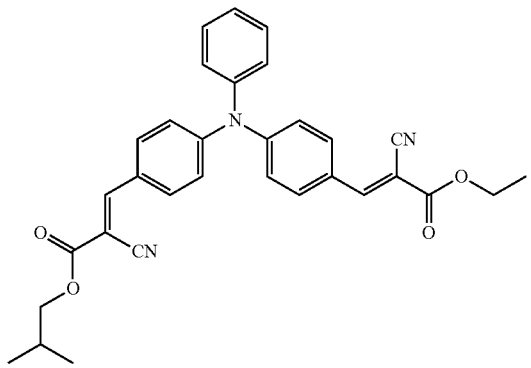
Compound No. 30
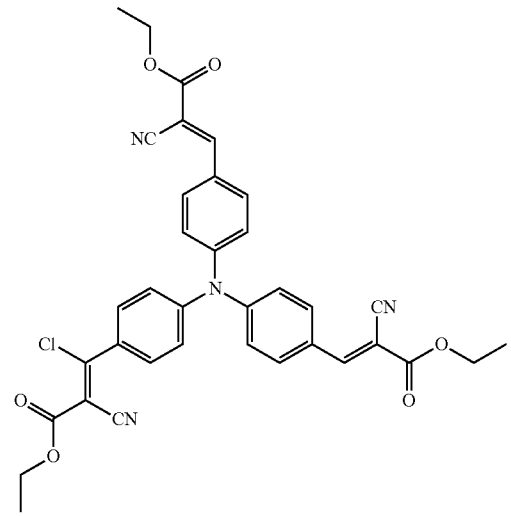
Compound No. 31
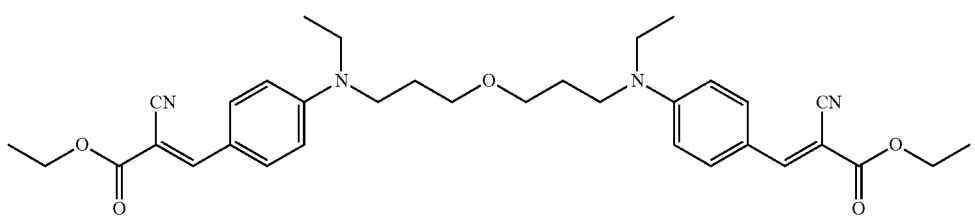
Compound No. 32
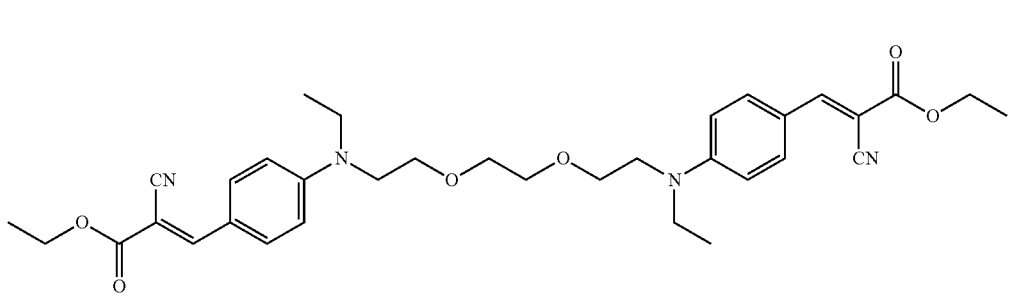
Compound No. 33
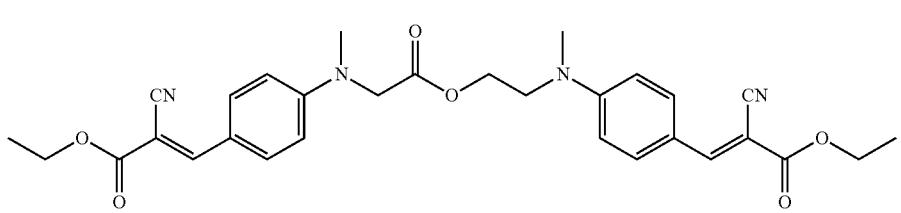
Compound No. 34
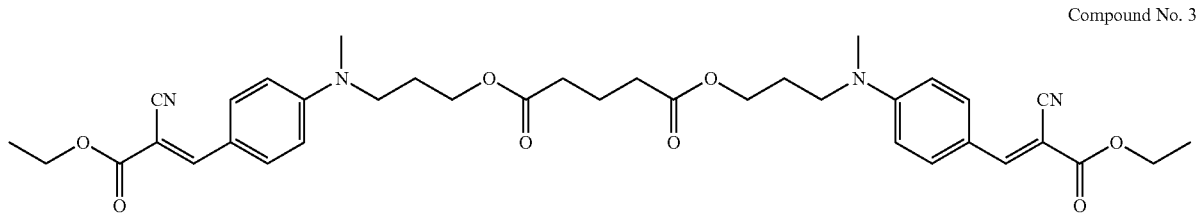

-continued
Compound No. 35
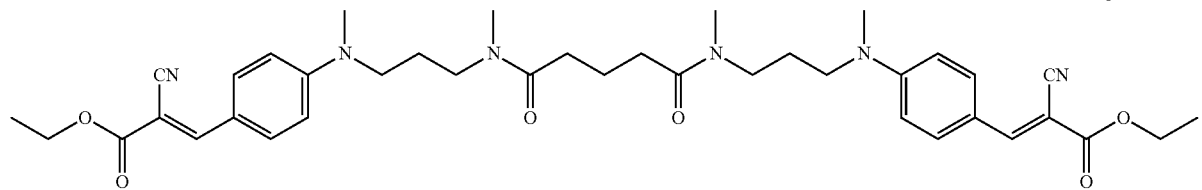
[Chemical Formula 25]
Compound No. 36
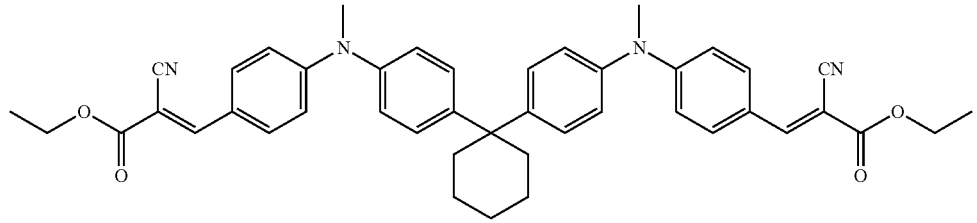
Compound No. 37
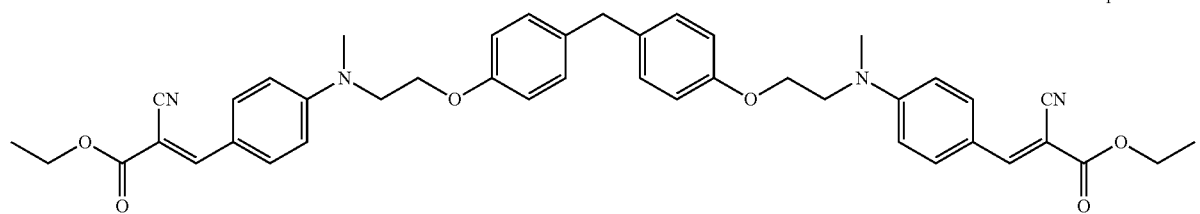
Compound No. 38
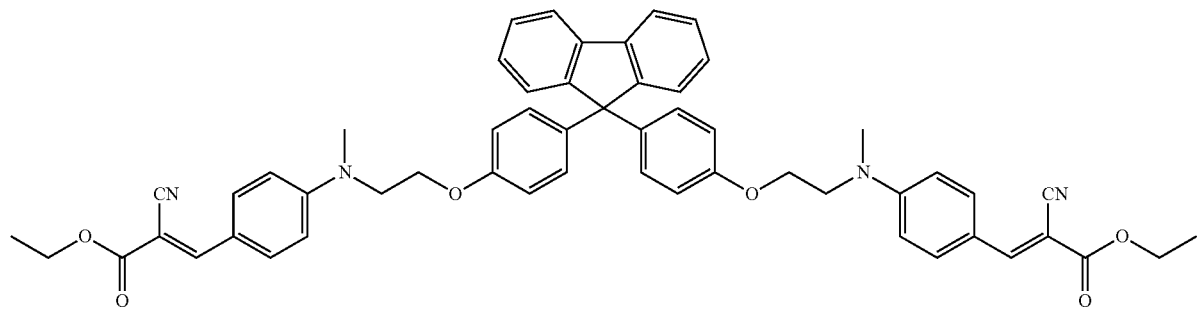
Compound No. 39
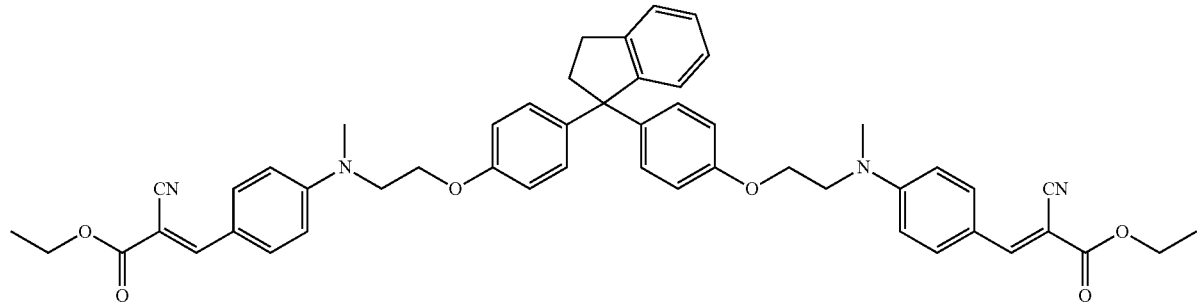

Compound No. 40
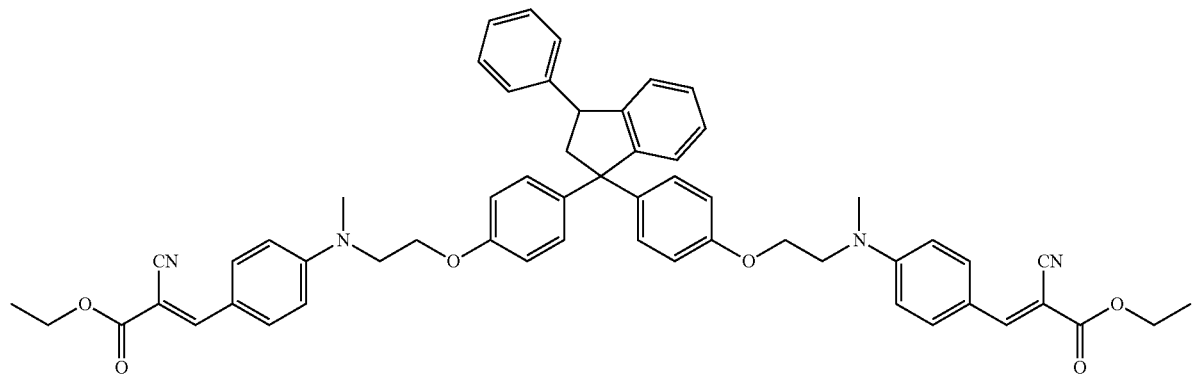
[Chemical Formula 26]
Compound No. 41
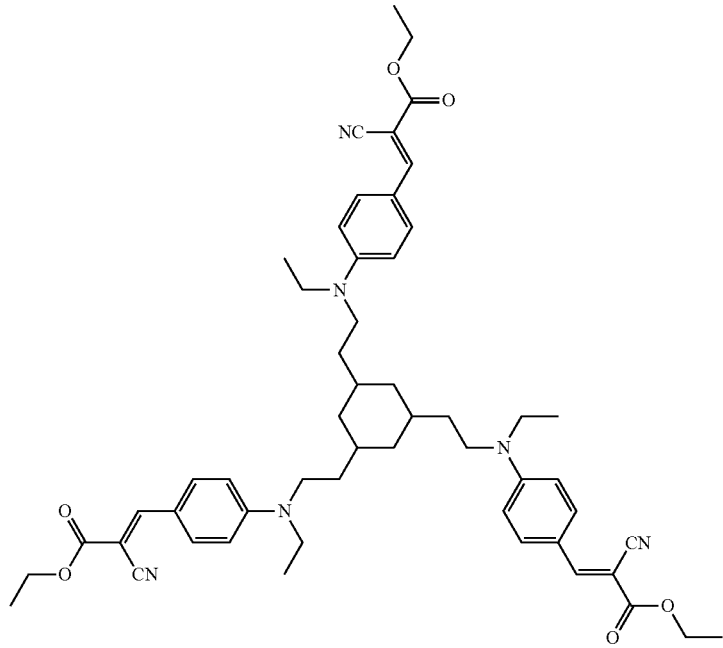
Compound No. 42        Compound No. 43
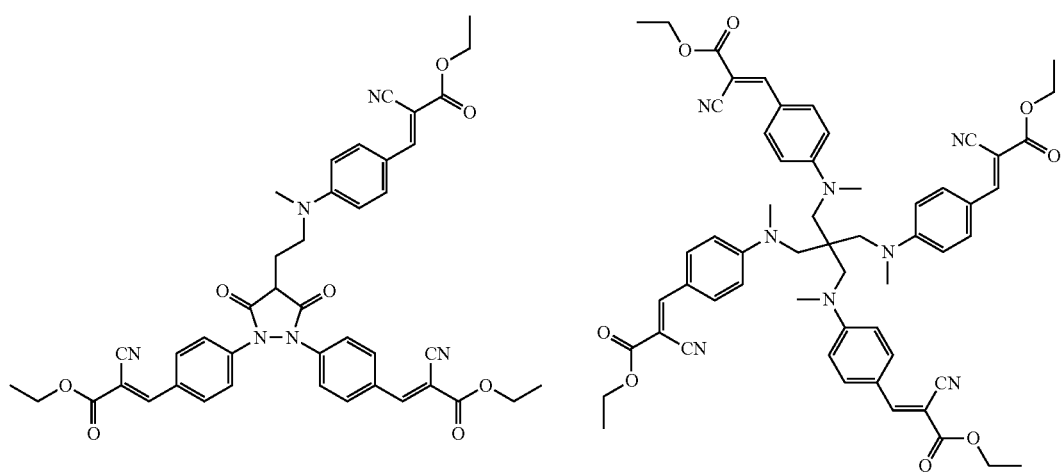

-continued
Compound No. 44
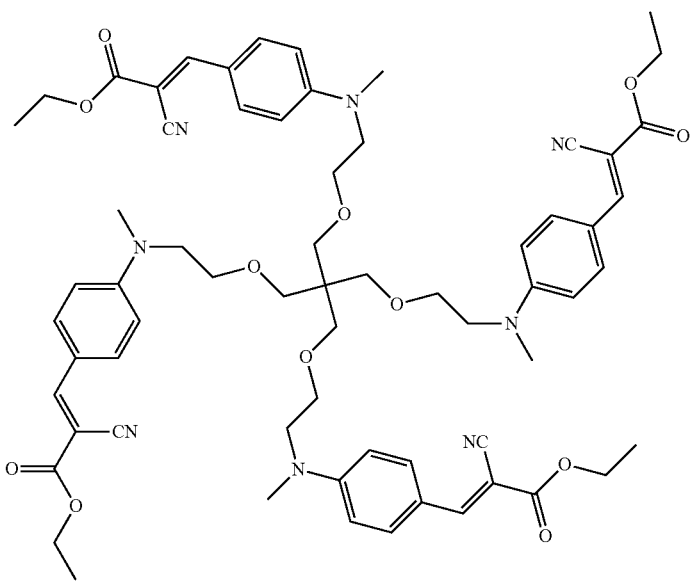
Compound No. 45
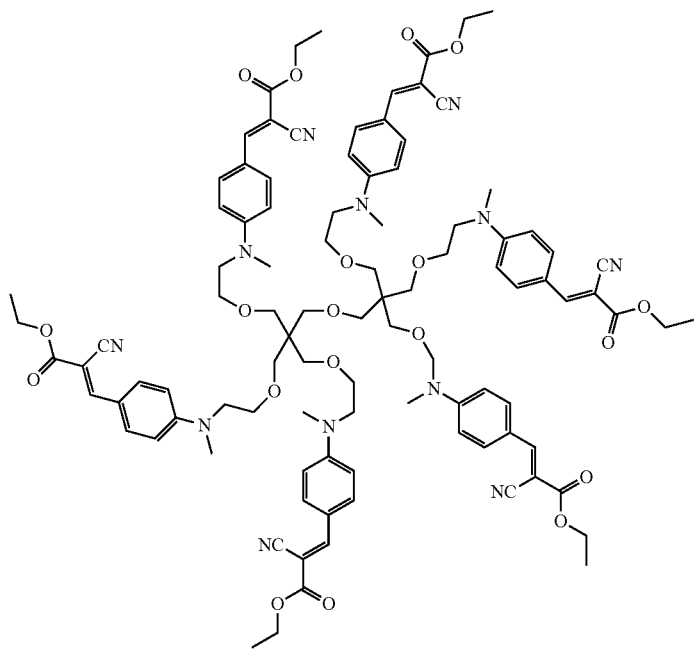
[Chemical Formula 27]
Compound No. 46
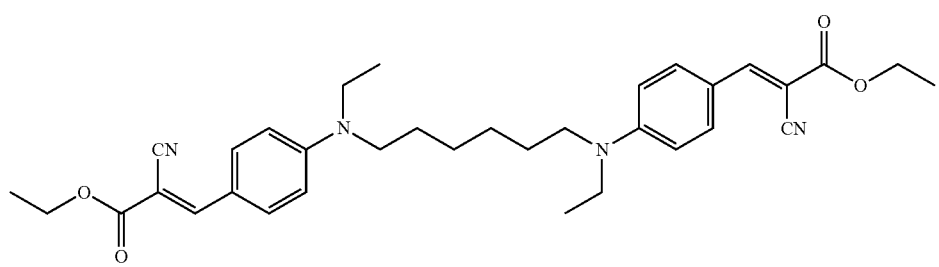

-continued
Compound No. 47
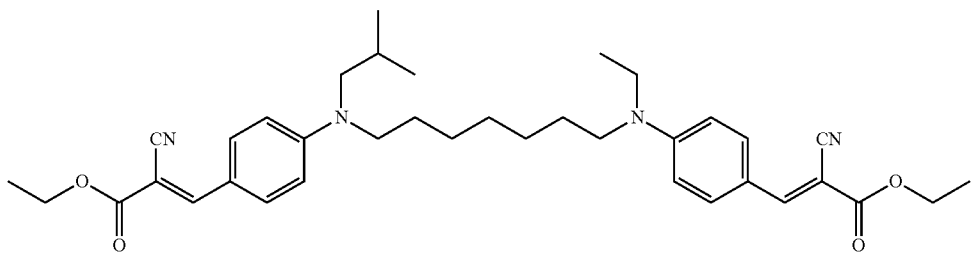
Compound No. 48
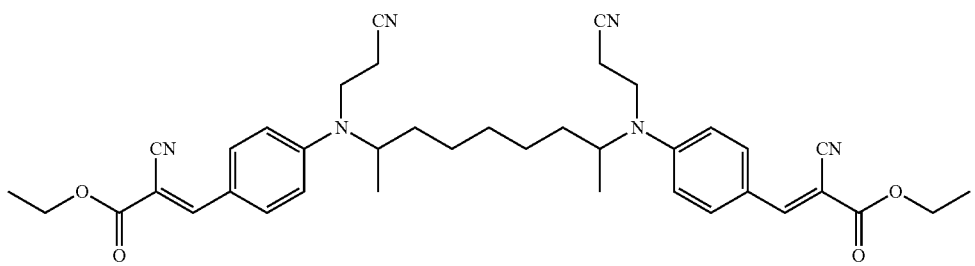
Compound No. 49
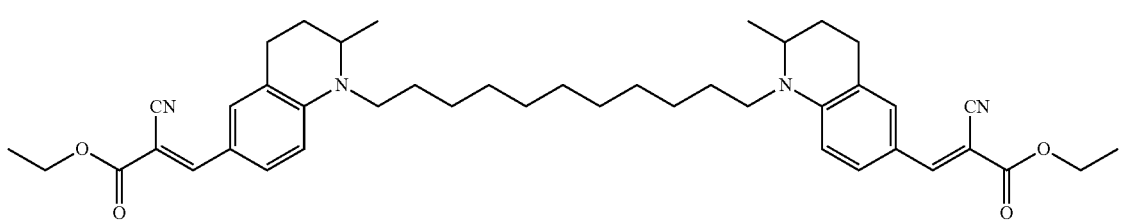
Compound No. 50
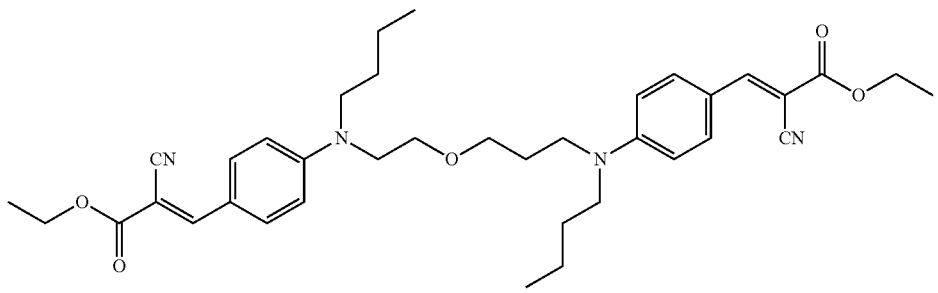
Compound No. 51
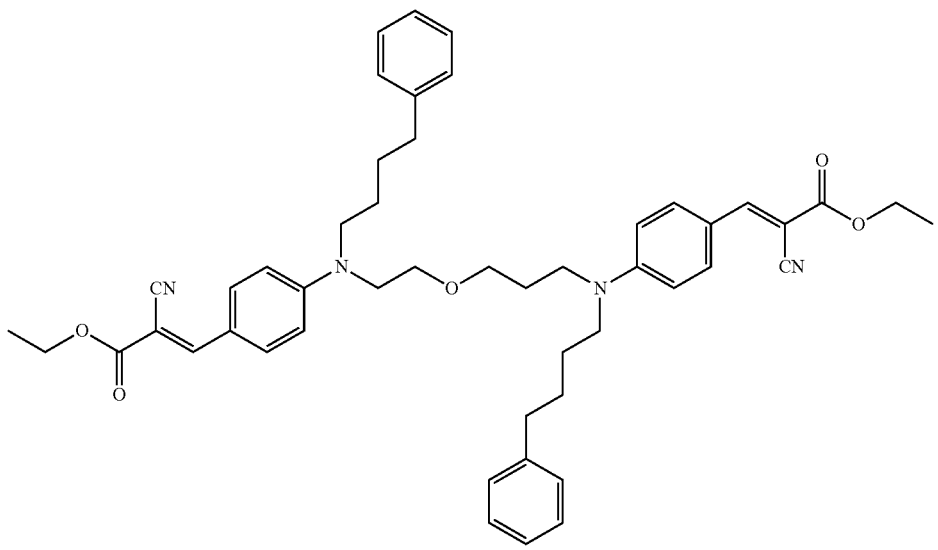

-continued
Compound No. 52
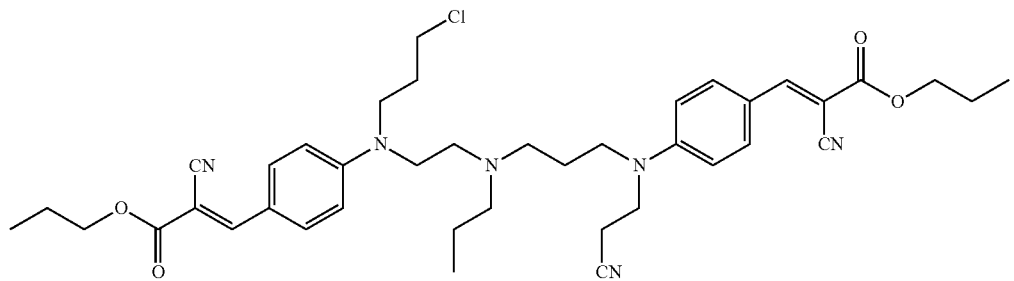
Compound No. 53
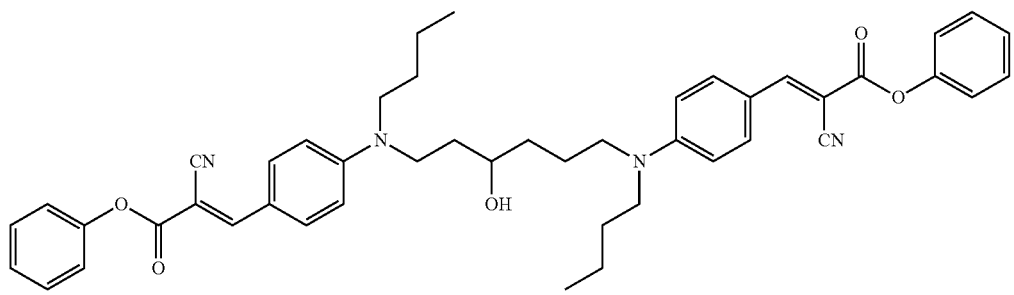
Compound No. 54
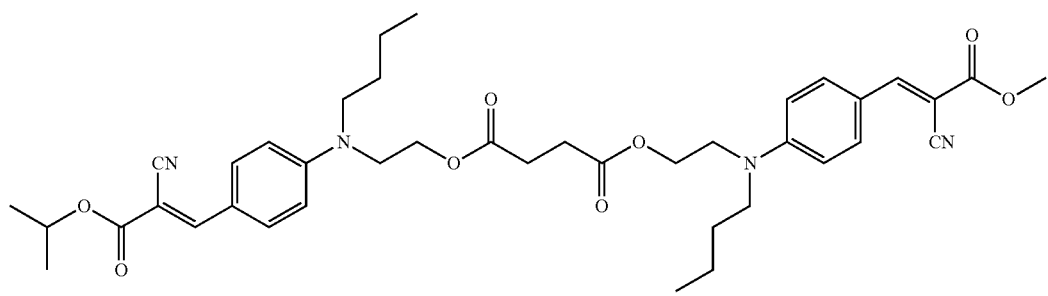
Compound No. 55
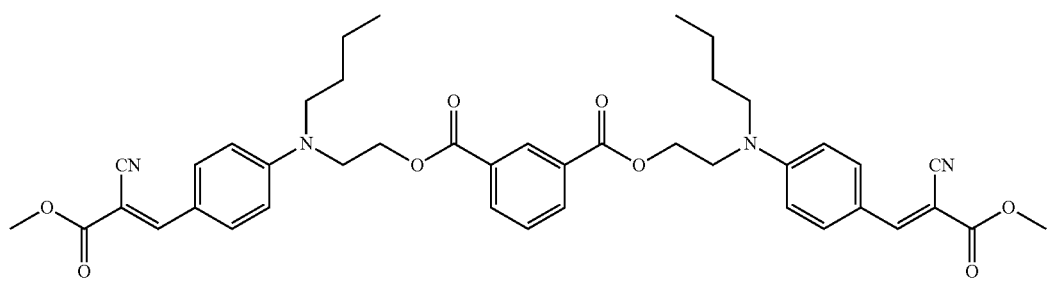
Compound No. 56
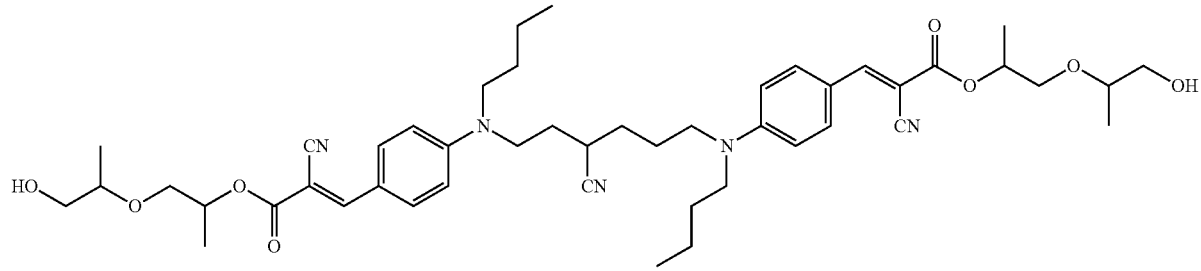

-continued
Compound No. 57
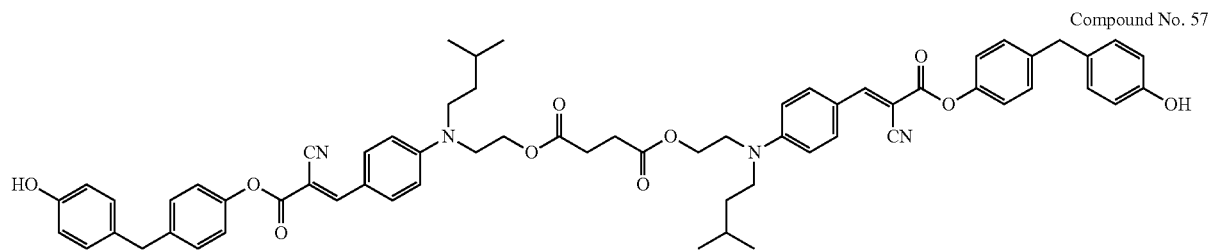
Compound No. 58
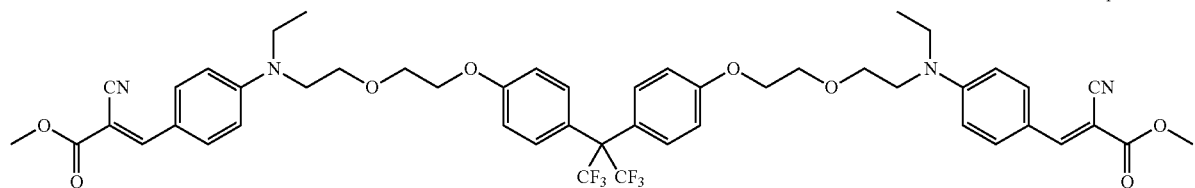
Compound No. 59
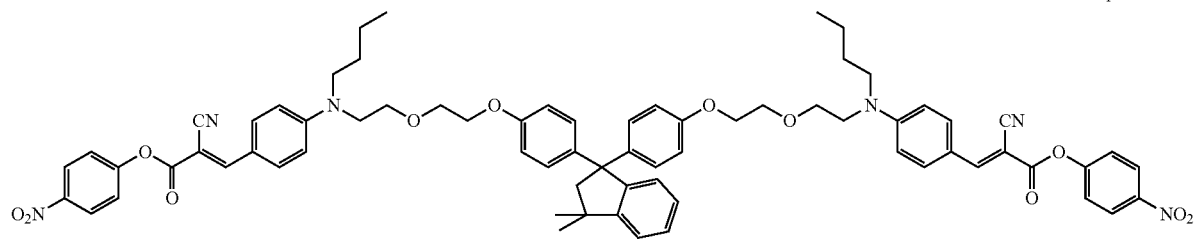
Compound No. 60
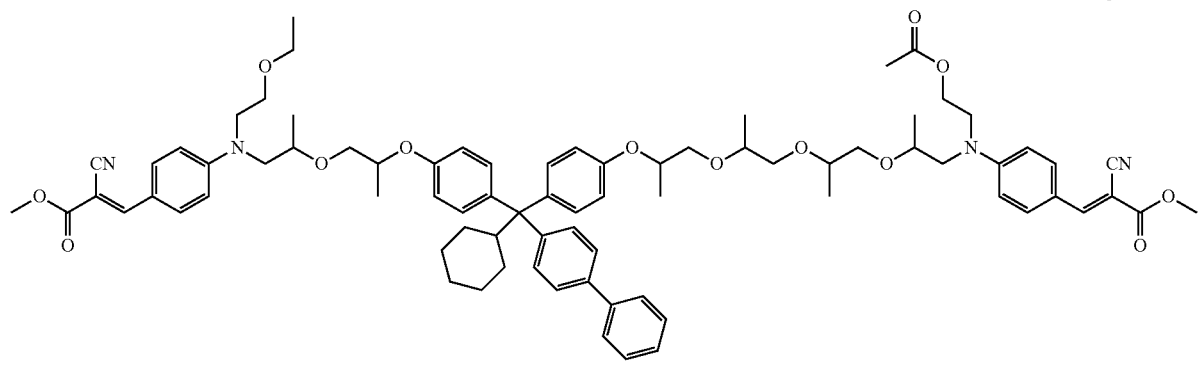
Compound No. 61
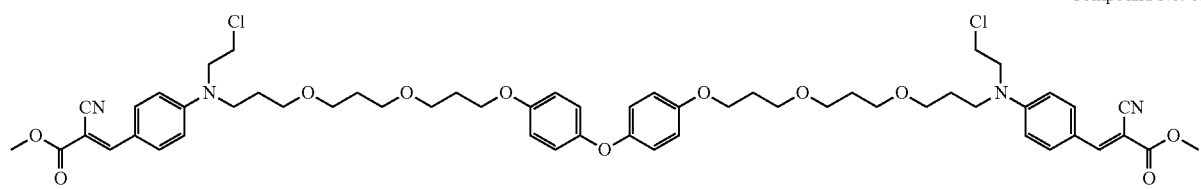
[Chemical Formula 28]
Compound No. 62
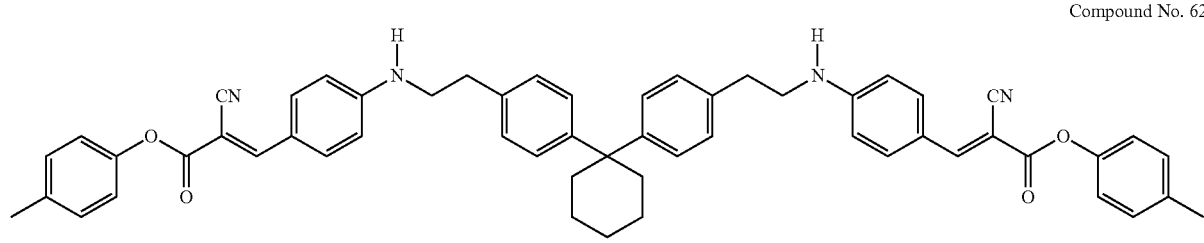

-continued
Compound No. 63
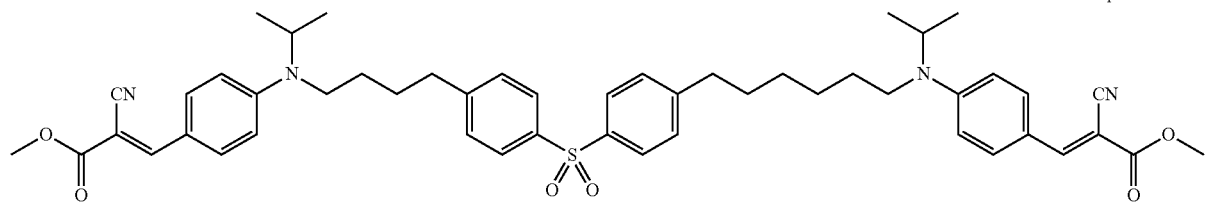
Compound No. 64
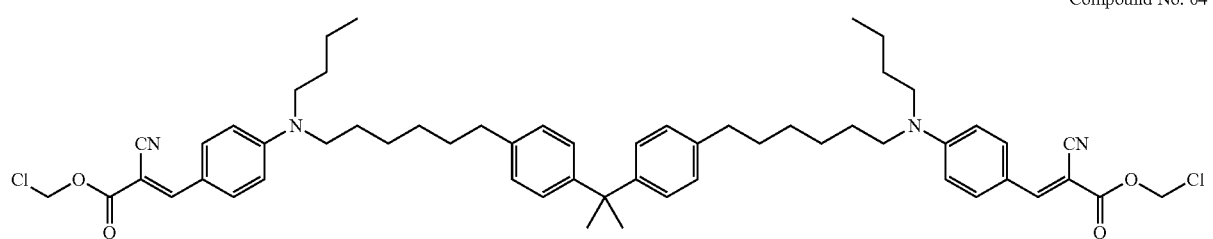
Compound No. 65
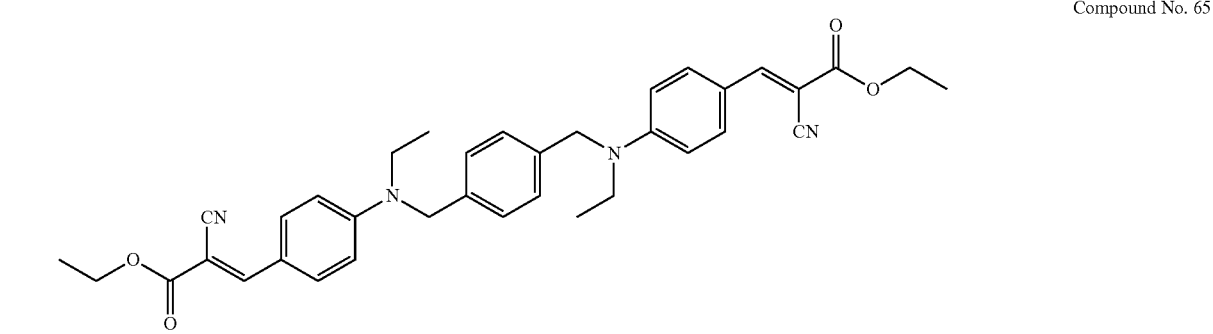
Compound No. 66
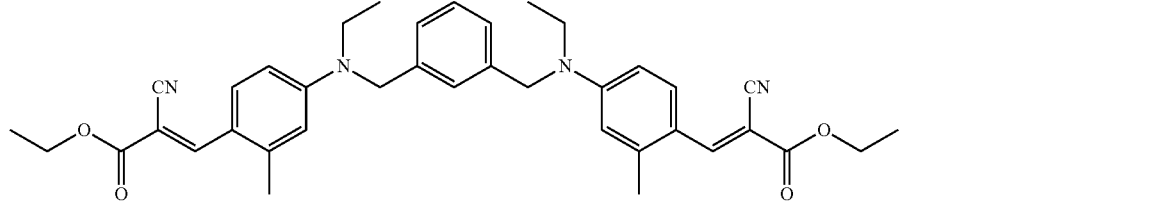
Compound No. 67
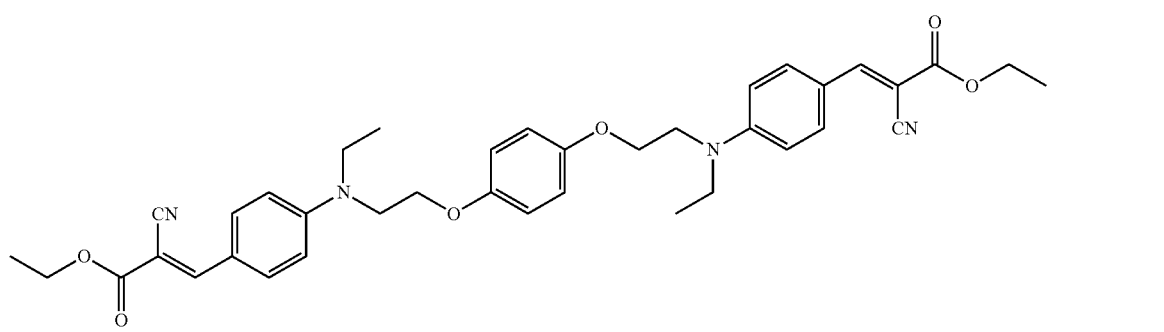
Compound No. 68
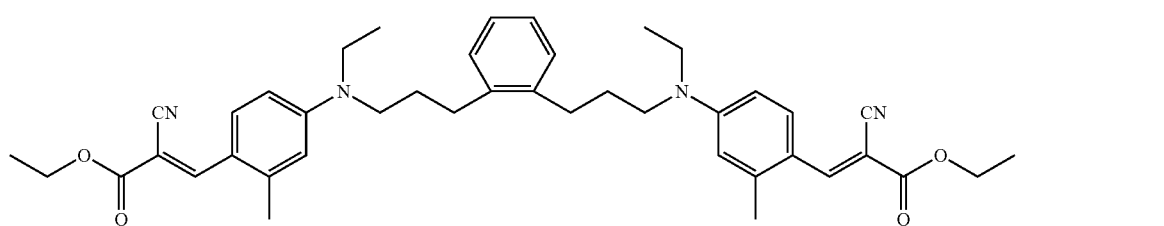

Compound No. 69
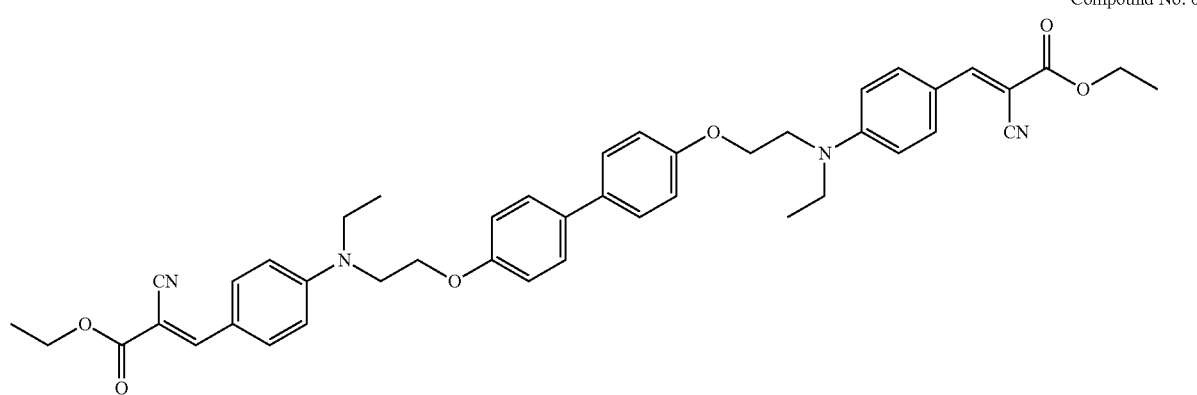
Compound No. 70
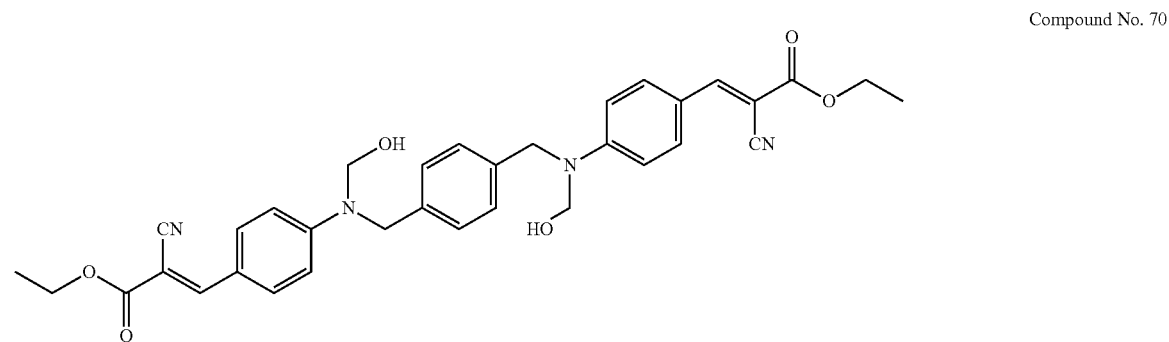
Compound No. 71
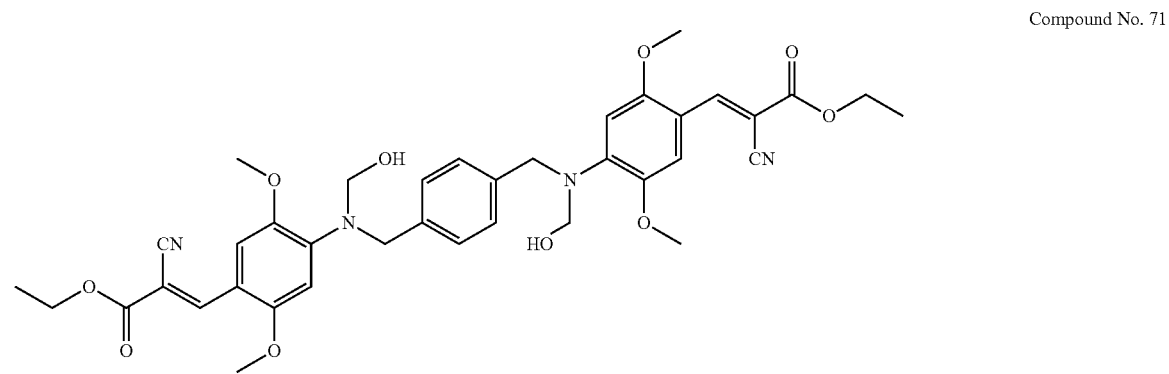
Compound No. 72
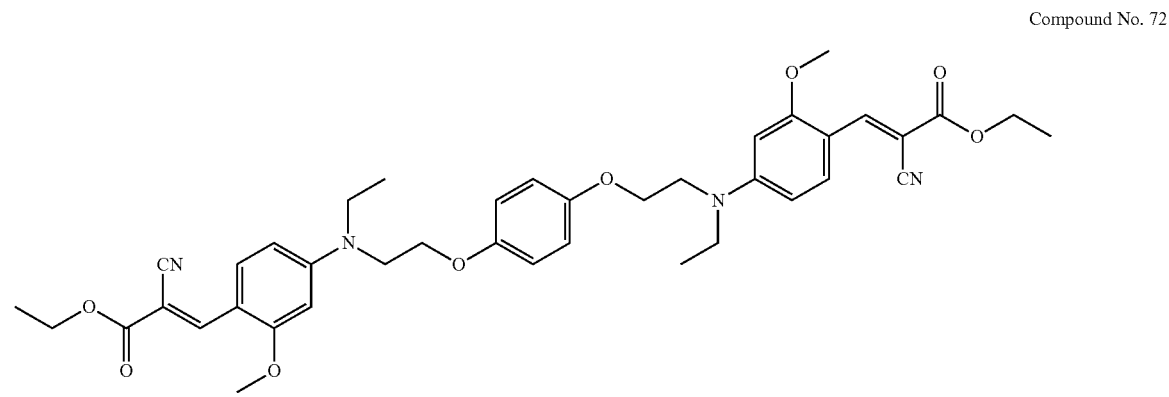

Compound No. 73
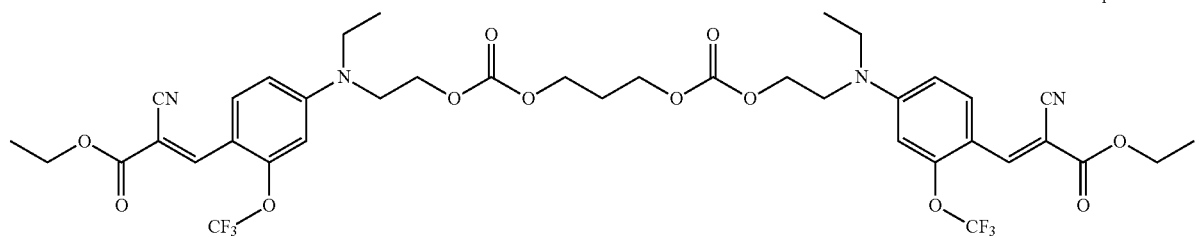
Compound No. 74
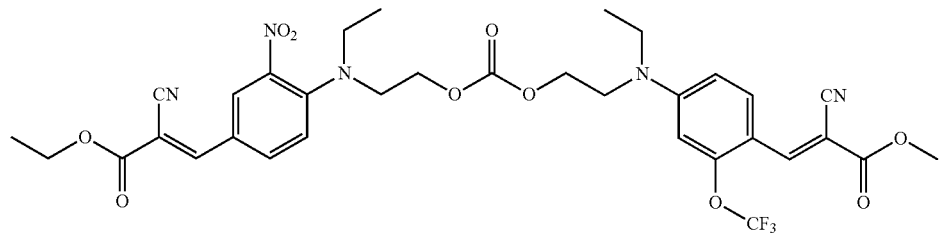
Compound No. 75
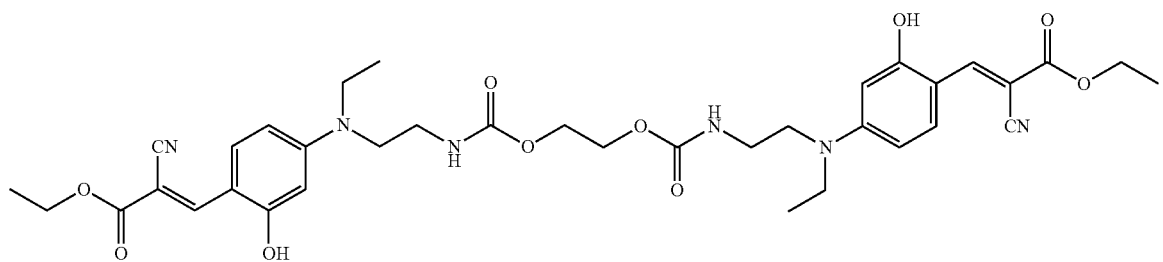
Compound No. 76
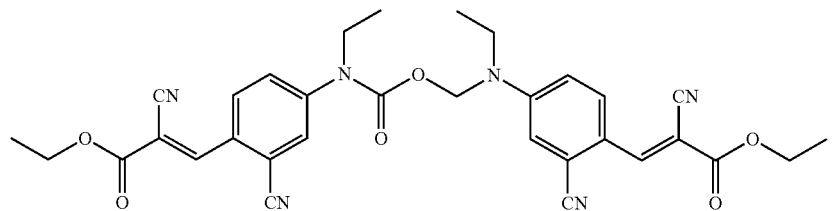
Compound No. 77
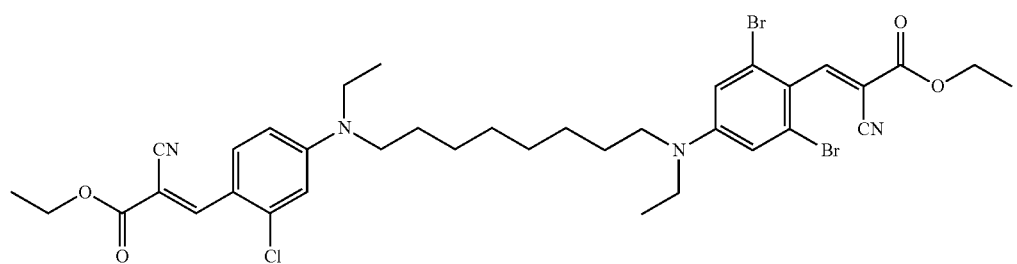
Compound No. 78
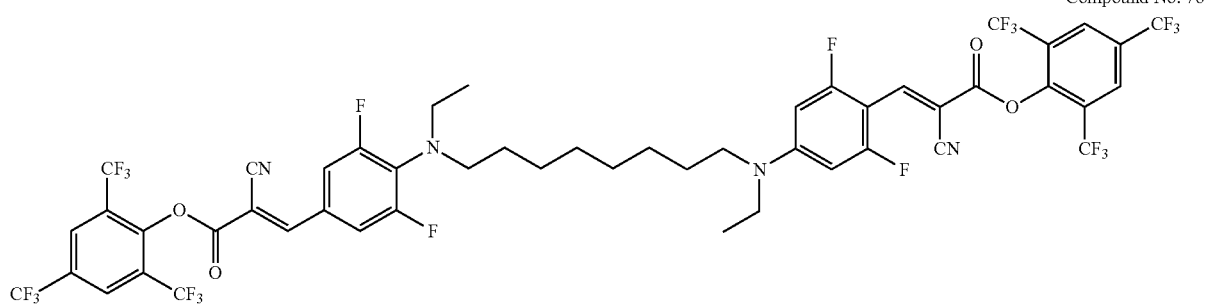

Compound No. 79
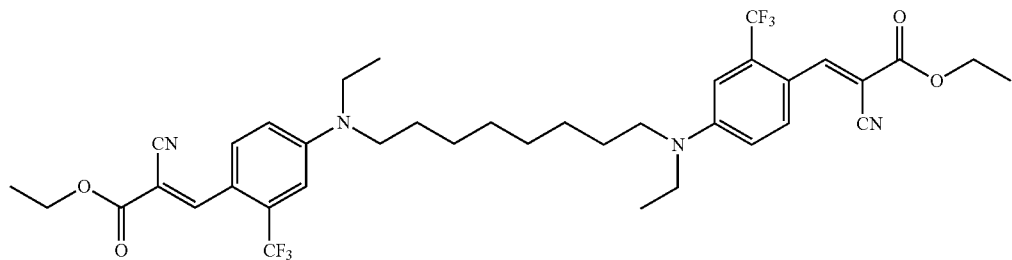
Compound No. 80
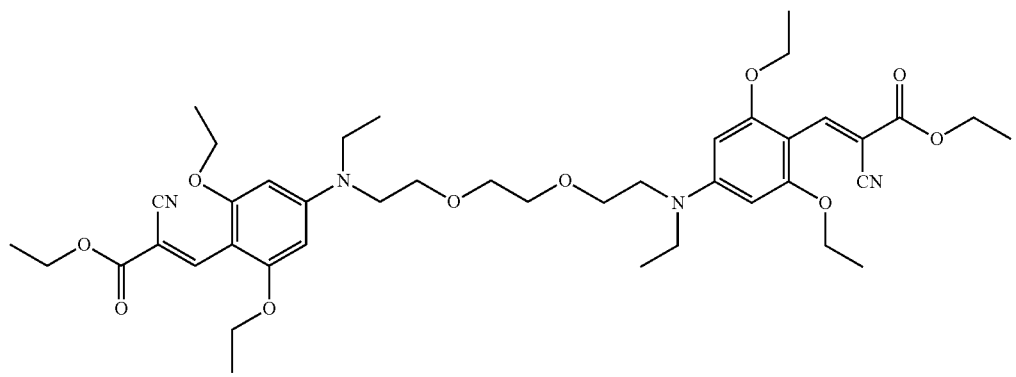
[Chemical Formula 29]
Compound No. 81
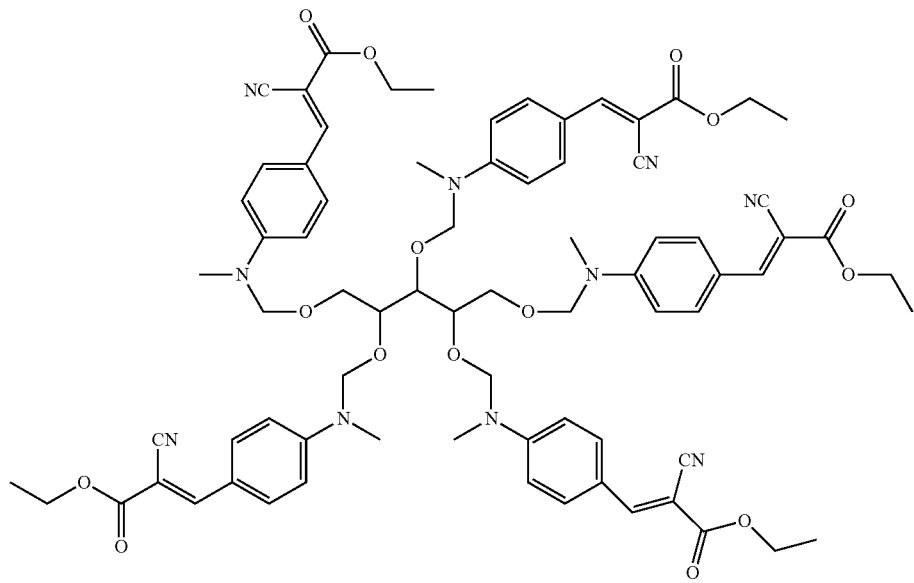

-continued
Compound No. 82
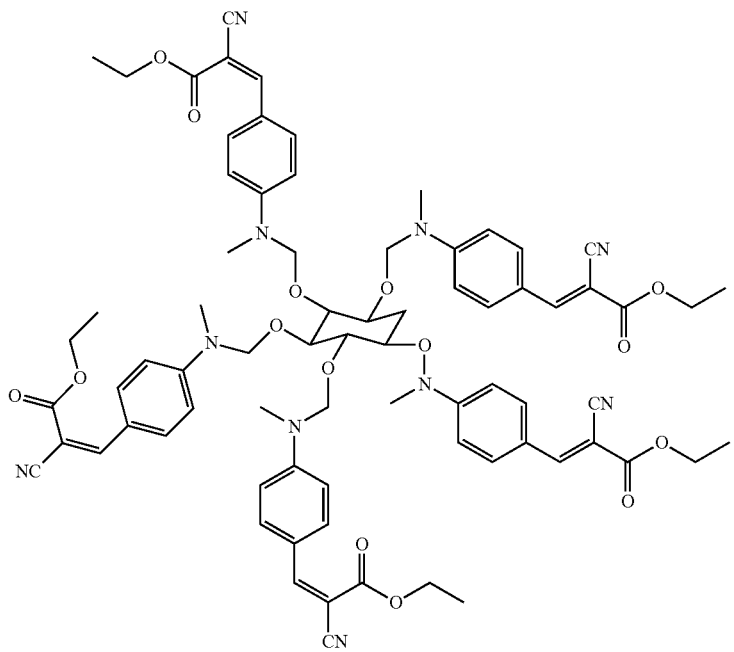
Compound No.83
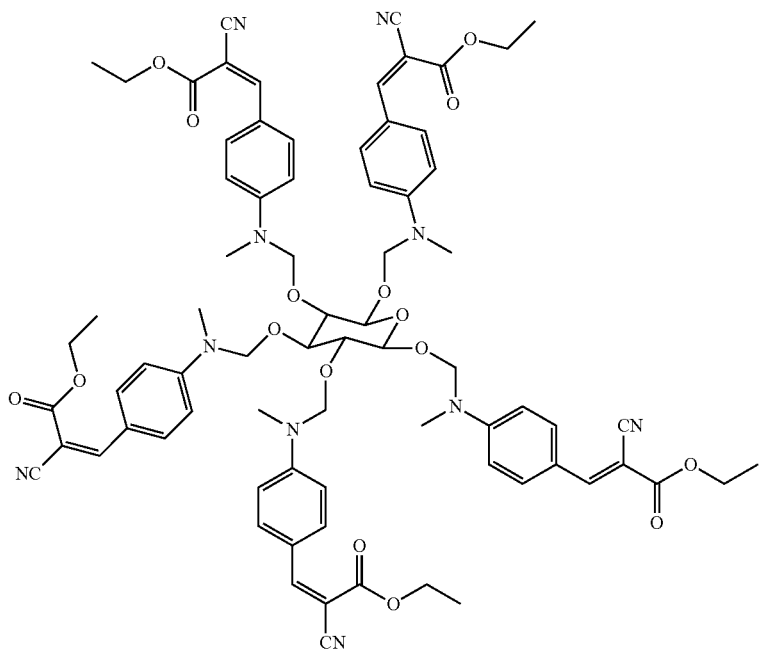

[Chemical Formula 30]
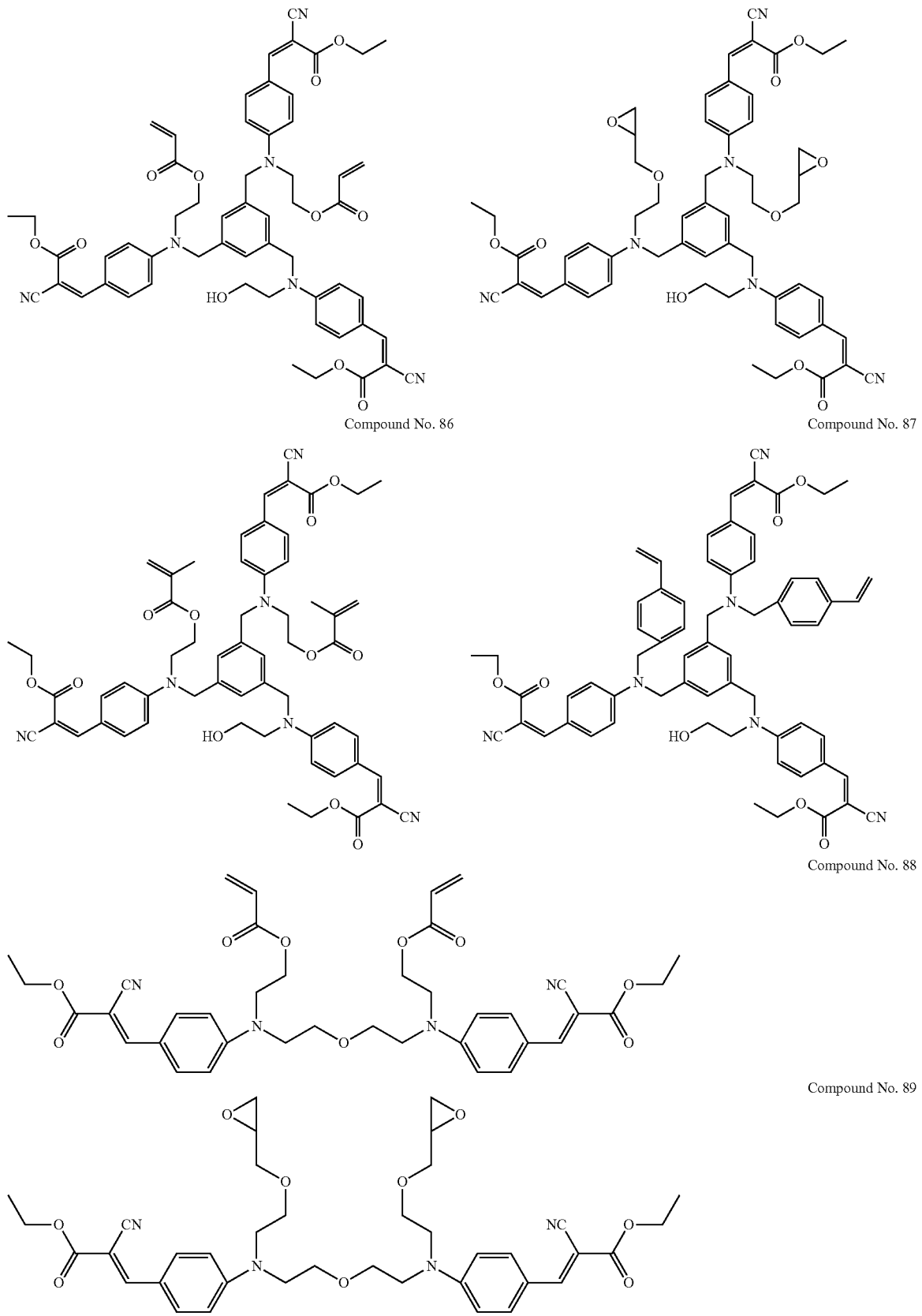

Although the method for the production of the compound represented by the above-mentioned general formula (1) is not specifically limited, for example, the compound can be produced according to the following reaction formula. Specifically, the compound represented by the above-mentioned general formula (1) can be obtained by reacting an aldehyde (9) and a cyanoacetic acid ester (10) under a basic condition.

[Chemical Formula 31]

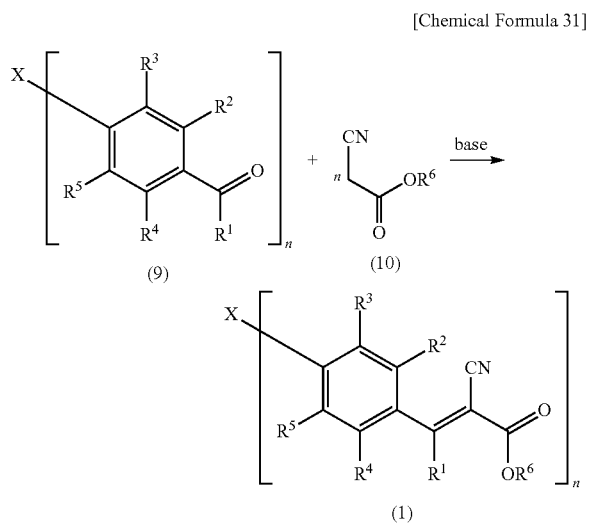

wherein in the above-mentioned formula, $R^1$ to $R^6$, X and n are similar to those in the general formula (1).

The novel compound of the present invention (the dye (A) of the present invention) is used as a colored photosensitive composition and a colored alkali-developable photosensitive composition mentioned below, and used in optical filters that are used in displays and optical lenses, photosensitive materials for silver halide photography, dyed products, coating materials, optical recording pigments and the like.

Next, the dye (A) of the present invention will be explained. For the points that are not specifically explained, the explanations made for the novel compound of the present invention will be suitably applied.

The dye (A) of the present invention only needs to contain at least one kind of the compound represented by the above-mentioned general formula (1), and a single dye or a combination of plural kinds can be used. Furthermore, it is possible to use a known dye besides the compound represented by the above-mentioned general formula (1). Examples of the known dye may include dyes such as azo dyes, anthraquinone dyes, indigoid dyes, triarylmethane dyes, xanthene dyes, alizarin dyes, acridine dyes, stilbene dyes, thiazole dyes, naphthol dyes, quinoline dyes, nitro dyes, indamine dyes, oxazine dyes, phthalocyanine dyes and cyanine dyes, and the like, and these may be used by mixing plural dyes.

In the dye (A) of the present invention, the content of the compound represented by the above-mentioned general formula (1) is preferably 50 to 100 mass %, more preferably 70 to 100 mass %. When the content of the compound represented by the above-mentioned general formula (1) is less than 50 mass %, the solubility in solvents may be decreased, or the heat-resistance may be decreased.

Next, the colored photosensitive composition and colored alkali-developable photosensitive composition (hereinafter also simply referred to as colored compositions) of the present invention will be explained. For the points that are not specifically explained, the explanations made for the dye (A) of the present invention are suitably applied.

The colored composition of the present invention contains the dye (A) of the present invention, (B) a polymerizable compound having an ethylenically unsaturated bond (including (B') a polymerizable compound having an ethylenically unsaturated bond, which has alkali-developability) and (C) a photopolymerization initiator, and further contains (D) an inorganic pigment and/or an organic pigment as necessary.

<Dye (A)>

The dye (A) of the present invention is as mentioned above. In the colored composition of the present invention, the content of the dye (A) of the present invention is preferably 0.01 to 50 mass %, more preferably 0.1 to 30 mass %. In the case when the content of the dye (A) is less than 0.01 mass %, a color of a desired concentration may not be obtained in the cured product of the present invention, whereas when the content is more than 50 mass %, precipitation of the dye (A) may occur in the colored composition.

<Polymerizable Compound Having Ethylenically Unsaturated Bond (B)>

The above-mentioned polymerizable compound having an ethylenically unsaturated bond (B) is not specifically limited, and those having been conventionally used in photosensitive compositions can be used, and examples may include unsaturated aliphatic hydrocarbons such as ethylene, propylene, butylene, isobutylene, vinyl chloride, vinylidene chloride, vinylidene fluoride and tetrafluoroethylene; unsaturated polybasic acids such as (meta)acrylic acid, α-chloroacrylic acid, itaconic acid, maleic acid, citraconic acid, fumaric acid, himic acid, crotonic acid, isocrotonic acid, vinyl acetate, allyl acetate, cinnamic acid, sorbic acid, mesaconic acid, mono[2-(meth)acryloyoxyethyl]succinate, mono[2-(meth)acryloyoxyethyl]phthalate, mono(meth)acrylates of polymers having a carboxy group and a hydroxyl group on the both terminals such as ω-carboxypolycaprolactone mono(meth)acrylate, hydroxyethyl(meth)acrylate maleate, hydroxypropyl(meth)acrylate maleate, dicyclopentadiene maleate or unsaturated polybasic acids such as multifunctional (meth)acrylates having one carboxyl group and two or more (meta)acryloyl groups; esters of unsaturated monobasic acids and polyhydric alcohols or polyhydric phenols such as 2-hydroxyethyl(meta)acrylate, 2-hydroxypropyl(meth)acrylate, glycidyl(meth)acrylate, the following compounds No. 121 to No. 124, methyl(meth)acrylate, butyl(meth)acrylate, isobutyl(meth)acrylate, t-butyl(meth)acrylate, cyclohexyl(meth)acrylate, n-octyl(meth)acrylate, isooctyl(meth)acrylate, isononyl(meth)acrylate, stearyl(meth)acrylate, lauryl(meth)acrylate, methoxyethyl(meth)acrylate, dimethylaminomethyl(meth)acrylate, aminoethyl(meth)acrylate, aminopropyl(meth)acrylate, dimethylaminopropyl(meth)acrylate, ethoxyethyl(meth)acrylate, poly(ethoxy)ethyl(meth)acrylate, butoxyethoxyethyl(meth)acrylate, ethyl hexyl(meth)acrylate, phenoxyethyl(meth)acrylate, tetrahydrofuryl(meth)acrylate, vinyl(meth)acrylate, allyl(meth)acrylate, benzyl(meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri(meth)acrylate, trimethylolpropane tri(meth)acrylate, dipentaerythritol penta(meth)acrylate, dipentaerythritol hexa(meth)acrylate, pentaerythritol tetra(meth)acrylate, pentaerythritol tri(meth)acrylate, tricyclodecanedimethylol di(meth)acrylate, tri[(meth)acryloylethyl]isocyanurate and polyester(meth)acrylate oligomer; metal salts of unsaturated polybasic acids such as zinc(meth)acrylate and magnesium(meth)acrylate; acid anhydrides of unsaturated polybasic acids such as maleic anhydride, itaconic anhydride, citraconic anhydride, methyltetrahydrophthalic anhydride, tetrahydrophthalic anhydride, trialkyltetrahydrophthalic anhydride, 5-(2,5-dioxotetrahydrofuryl)-3-methyl-3-cyclohexene-1,2-dicarboxylic anhydride, trialkyltetrahydrophthalic anhydride-maleic anhydride additive, dodecenyl succinic anhydride and methylhimic anhydride; amides of unsaturated monobasic acids and polyvalent amines such as (meth)acrylamide, methylene bis-(meth)acrylamide, diethylenetriamine tris(meth)acrylamide, xylylene bis(meth)acrylamide, α-chloroacrylamide and N-2-hydroxyethyl(meth)acrylamide; unsaturated aldehydes such as acrolein; unsaturated nitriles such as (meth)acrylonitrile, α-chloroacrylonitrile, vinylidene cyanide and allyl cyanide; unsaturated aromatic compounds such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether and vinylbenzyl glycidyl ether; unsaturated ketones such as methyl vinyl ketone; unsaturated amine compounds such as vinylamine, allylamine, N-vinylpyrrolidone and vinylpiperidine; vinyl alcohols such as allyl alcohol and crotyl alcohol; vinyl ethers such as vinyl methyl ether, vinyl ethyl ether, n-butyl vinyl ether, isobutyl vinyl ether and allyl glycidyl ether; unsaturated imides such as maleimide, N-phenylmaleimide and N-cyclohexylmaleimide; indenes such as indene and 1-methylindene; aliphatic conjugate dienes such as 1,3-butadiene, isoprene and chloroprene; macromonomers having mono(meth)acryloyl groups on the terminals of polymer molecule chains such as polystyrene, polymethyl(meth)acrylate, poly-n-butyl(meth)acrylate and polysiloxane; vinylurethane compounds of vinyl chloride, vinylidene chloride, divinyl succinate, diallyl phthalate, triallyl phosphate, triallyl isocyanurate, vinylthioether, vinylimidazole, vinyloxazoline, vinylcarbazole, vinylpyrrolidone, vinylpyridine, hydroxyl group-containing vinyl monomers and polyisocyanate compounds, vinylepoxy compounds of hydroxyl group-containing vinyl monomers and polyepoxy compounds, reaction products of hydroxyl group-containing multifunctional acrylates such as pentaerythritol triacrylate and dipentaerythritol pentaacrylate and multifunctional isocyanates such as trylene diisocyanate and hexamethylene diisocyanate, multifunctional acrylates having an acid value, which are reaction products of hydroxyl group-containing multifunctional acrylates such as pentaerythritol triacrylate and dipentaerythritol pentaacrylate and dibasic acid anhydrides such as succinic anhydride, phthalic anhydride and tetrahydrophthalic anhydride.

These polymerizable compounds can be used alone or by mixing two or more kinds, and in the case when two or more kinds are mixed and used, those may be co-polymerized in advance and used as a copolymer.

[Chemical Formula 32]

Compound No. 121

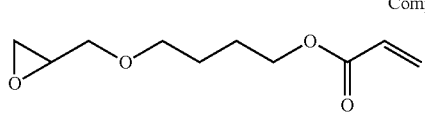

[Chemical Formula 33]

Compound No. 122

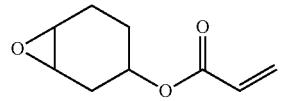

[Chemical Formula 34]

Compound No. 123

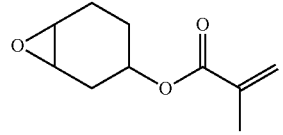

[Chemical Formula 35]

Compound No. 124

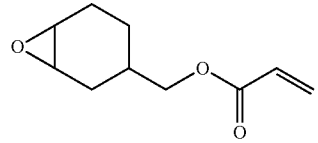

Furthermore, when (B') a polymerizable compound having an ethylenically unsaturated bond, which has alkali-developability (hereinafter also referred to as (B') an alkali-developable compound having an ethylenically unsaturated bond) is used as the above-mentioned polymerizable compound having an ethylenically unsaturated bond (B) in the colored composition of the present invention, the colored photosensitive composition of the present invention becomes a colored alkali-developable photosensitive composition. Examples of the alkali-developable compound having an ethylenically unsaturated bond (B') may include (meth)acrylic acid esters such as (meth)acrylic acid, methyl(meth)acrylate, ethyl (meth)acrylate, propyl(meth)acrylate, isopropyl(meth)acrylate, butyl(meth)acrylate, isobutyl(meth)acrylate, t-butyl (meth)acrylate, benzyl(meth)acrylate, phenyl(meth)acrylate, cyclohexyl(meth)acrylate, phenoxyethyl(meth)acrylate, 2-ethylhexyl(meth)acrylate, isobornyl(meth)acrylate, 2-hydroxyethyl(meth)acrylate and tetrahydrofurfuryl(meth)acrylate; N-vinylpyrrolidone; styrenes such as styrene and derivatives thereof, and α-methylstyrene; acrylamides such as (meth)acrylamide, methylol(meth)acrylamide, alkoxymethylol(meth)acrylamide and diacetone(meth)acrylamide; copolymers of other vinyl compounds such as (meth)acrylonitrile, ethylene, propylene, butylene, vinyl chloride and vinyl acetate, and macromonomers such as polymethylmethacrylate macromonomers and polystyrene macromonomers, monomethacrylate of a tricyclodecane backbone, N-phenylmaleimide, methacryloyloxymethyl-3-ethyloxetane, and the like, with (meth)acrylic acid, and copolymers of (meth)acrylic acid obtained by reacting these with isocyanate compounds having an unsaturated bond such as KARENZ MOI and AOI manufactured by Showa Denko K. K., and novolak-type epoxy compounds such as phenol and/or cresol novolak epoxy resins, novolak epoxy resins having biphenyl backbones or naphthalene backbones, bisphenol A novolak-type epoxy compounds and dicyclopentadiene novolak-type epoxy compounds, polyphenylmethane-type epoxy resins having multifunctional epoxy groups, and resins obtained by reacting the epoxy groups of the epoxy compound represented by the following general formula (I) or the like with an unsaturated monobasic acid, and further reacting with a polybasic acid anhydride, can be used. These monomers can be used by one kind alone, or by mixing two or more kinds.

Furthermore, it is preferable that the above-mentioned alkali-developable compound having an ethylenically unsaturated bond contains an unsaturated group by 0.2 to 1.0 equivalent amount.

[Chemical Formula 36]

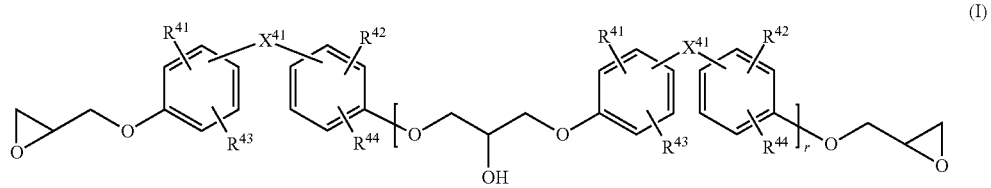

(I)

wherein in the formula, $X^{41}$ represents a direct bond, a methylene group, an alkylidene group having 1 to 4 carbon atom(s), an alicyclic hydrocarbongroup having 3 to 20 carbon atoms, —O—, —S—, —SO$_2$—, —SS—, —SO—, —CO—, —OCO— or a substituent represented by each of the above-mentioned [Chemical Formula 3] to [Chemical Formula 5], wherein the alkylidene group may be substituted with halogen atom(s), $R^{41}$, $R^{42}$, $R^{43}$ and $R^{44}$ each independently represents a hydrogen atom, an alkyl group having 1 to 5 carbon atom(s), an alkoxy group having 1 to 8 carbon atom(s), an alkenyl group having 2 to 5 carbon atoms or a halogen atom, wherein the above-mentioned alkyl group, alkoxy group and alkenyl group may be substituted with halogen atom(s), and r is an integer of 0 to 10.

Examples of the above-mentioned unsaturated monobasic acid that is reacted with the epoxy groups of the above-mentioned epoxy compound may include acrylic acid, methacrylic acid, crotonic acid, cinnamic acid, sorbic acid, hydroxyethyl methacrylate maleate and the like. Examples may include hydroxyethyl acrylate maleate, hydroxypropyl methacrylate maleate, hydroxypropyl acrylate maleate, dicyclopentadiene maleate and the like.

Furthermore, examples of the above-mentioned polybasic acid anhydride that is reacted after reacting the above-mentioned unsaturated monobasic acid may include biphenyltetracarboxylic dianhydride, tetrahydrophthalic anhydride, succinic anhydride, maleic anhydride, trimellitic anhydride, pyromellitic anhydride, 2,2'-3,3'-benzophenonetetracarboxylic anhydride, ethylene glycol bisanhydrotrimellitate, glycerol trisanhydrotrimellitate, hexahydrophthalic anhydride, methyltetrahydrophthalic anhydride, nadic anhydride, methylnadic anhydride, trialkyltetrahydrophthalic anhydride, hexahydrophthalic anhydride, 5-(2,5-dioxotetrahydrofuryl)-3-methyl-3-cyclohexene-1,2-dicarboxylic anhydride, trialkyltetrahydrophthalic anhydride-maleic anhydride additive, dodecenylsuccinic anhydride, methylhimic anhydride and the like.

It is preferable that the reaction molar ratio of the above-mentioned epoxy compound, the above-mentioned unsaturated monobasic acid and the above-mentioned polybasic acid anhydride is preset as follows. Specifically, it is preferable that the ratio is such that, in an epoxy additive having a structure in which 0.1 to 1.0 carboxyl group of the above-mentioned unsaturated monobasic acid is added to one epoxy group of the above-mentioned epoxy compound, the acid anhydride structure of the above-mentioned polybasic acid anhydride becomes 0.1 to 1.0 with respect to one hydroxyl group of the epoxy additive.

The reaction of the above-mentioned epoxy compound, the above-mentioned unsaturated monobasic acid and the above-mentioned polybasic acid anhydride can be conducted according to a conventional method.

In order to adjust the acid value to thereby improve the developability of the colored alkali-developable photosensitive composition of the present invention, a monofunctional or multifunctional epoxy compound can further be used together with the above-mentioned alkali-developable compound having an ethylenically unsaturated bond. The above-mentioned alkali-developable compound having an ethylenically unsaturated bond preferably has an acid value of the solid content within the range of 5 to 120 mg KOH/g, and it is preferable that the use amount of the monofunctional or multifunctional epoxy compound is selected so as to satisfy the above-mentioned acid value.

Examples of the above-mentioned monofunctional epoxy compound may include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxyglycidyl ether, p-butylphenol glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxylated soybean oil, epoxylated linseed oil, glycidyl butyrate, vinylcyclohexane monoxide, 1,2-epoxy-4-vinylcyclohexane, styrene oxide, pinene oxide, methylstyrene oxide, cyclohexene oxide, propylene oxide, the above-mentioned compounds No. 122 and No. 123, and the like.

As the above-mentioned multifunctional epoxy compound, it is preferable to use one or more kinds selected from the group consisting of bisphenol-type epoxy compounds and glycidyl ethers, since a colored alkali-developable photosensitive composition having finer properties can be obtained. As the bisphenol-type epoxy compound, the epoxy compound represented by the above-mentioned general formula (I) can be used, and for example, bisphenol-type epoxy compounds such as hydrogenated bisphenol-type epoxy compounds can also be used. Examples of the glycidyl ethers may include ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1- tri(glycidyloxymethyl)ethane, 1,1,1-tri(glycidyloxymethyl)methane, 1,1,1,1-tetra(glycidyloxymethyl)methane and the like.

In addition, novolak-type epoxy compounds such as phenol novolak-type epoxy compounds, biphenyl novolak-type epoxy compounds, cresol novolak-type epoxy compounds, bisphenol A novolak-type epoxy compounds and dicyclopentadiene novolak-type epoxy compounds; alicyclic epoxy compounds such as 3,4-epoxy-6-methylcyclohexylmethyl-3,4-epoxy-6-methylcyclohexane carboxylate, 3,4-epoxycyclohexylmethyl-3,4-epoxycyclohexane carboxylate and 1-epoxyethyl-3,4-epoxycyclohexane; glycidyl esters such as phthalic acid diglycidyl ester, tetrahydrophthalic acid diglycidyl ester and dimer acid glycidyl ester; glycidylamines such as tetraglycidyldiaminodiphenylmethane, triglycidyl-p-aminophenol and N,N-diglycidylaniline; heterocyclic epoxy compounds such as 1,3-diglycidyl-5,5-dimethylhydantoin and triglycidyl isocyanurate; dioxide compounds such as dicyclopentadiene dioxide; naphthalene-type epoxy compounds, triphenylmethane-type epoxy compounds, dicyclopentadiene-type epoxy compounds, and the like can be used.

In the colored composition of the present invention, it is preferable that the content of the above-mentioned polymerizable compound having an ethylenically unsaturated bond (B) (including the above-mentioned alkali-developable compound having an ethylenically unsaturated bond (B')) is 30 to 99 mass %, specifically 60 to 95 mass % in the colored composition of the present invention. When the content of the above-mentioned polymerizable compound having an ethylenically unsaturated bond (B) is less than 30 mass %, the cured product has insufficient kinetic strength, and thus cracks may be generated, and developing failure may occur in the case that the compound has alkali-developability, whereas when the content is more than 99 mass %, curing by exposure to light becomes insufficient, and tacks may be generated, and in the case when the compound has alkali-developability, the developing time becomes longer, and film defect may occur by the alkali on the cured part.

<Photopolymerization Initiator (C)>

As the above-mentioned photopolymerization initiator (C), a conventionally-known compound can be used, and examples may include benzophenone, phenyl biphenyl ketone, 1-hydroxy-1-benzoylcyclohexane, benzoin, benzyl dimethyl ketal, 1-benzyl-1-dimethylamino-1-(4'-morpholinobenzoyl)propane, 2-morpholyl-2-(4'-methylmercapto)benzoylpropane, thioxanthone, 1-chloro-4-propoxythioxanthone, isopropylthioxanthone, diethylthioxanthone, ethylanthraquinone, 4-benzoyl-4'-methyldiphenylsulfide, benzoin butyl ether, 2-hydroxy-2-benzoylpropane, 2-hydroxy-2-(4'-isopropyl)benzoylpropane, 4-butylbenzoyltrichloromethane, 4-phenoxybenzoyldichloromethane, benzoyl methyl formate, 1,7-bis(9'-acrydinyl)heptane, 9-n-butyl-3,6-bis(2'-morpholinoisobutyroyl)carbazole, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2,2-bis(2-chlorophenyl)-4,5,4',5'-tetraphenyl-1-2'-biimidazole, 4,4-azobisisobutyronitrile, triphenylphosphine, camphorquinone, benzoyl peroxide and the like, and examples of commercially available products may include N-1414, N-1717, N-1919, PZ-408, NCI-831, NCI-930 (manufactured by ADEKA Corporation), IRGACURE369, IRGACURE907, IRGACURE OXE 01, IRGACURE OXE 02 (manufactured by BASF), and the like.

In the colored composition of the present invention, it is preferable that the content of the above-mentioned photopolymerization initiator (C) is 0.1 to 30 mass %, specifically 0.5 to 10 mass % in the colored composition of the present invention. When the content of the above-mentioned photopolymerization initiator (C) is less than 0.1 mass %, curing by exposing to light may become insufficient, whereas when the content is more than 30 mass %, the initiator (C) may precipitate in the resin composition.

<Inorganic Pigment and/or Organic Pigment (D)>

An inorganic pigment and/or an organic pigment (D) may further be incorporated in the colored composition of the present invention. These pigments can be used alone or by mixing two or more kinds.

As the above-mentioned inorganic pigment and/or organic pigment (D), for example, inorganic pigments or organic pigments such as nitroso compounds, nitro compounds, azo compounds, diazo compounds, xanthene compounds, quinoline compounds, anthraquinone compounds, coumarin compounds, phthalocyanine compounds, isoindolinone compounds, isoindoline compounds, quinacridone compound, anthanthrone compounds, perynone compounds, perylene compounds, diketopyrolopyrrole compounds, thioindigo compounds, dioxazine compounds, triphenylmethane compounds, quinophthalone compounds and naphthalenetetracarboxylic acid; metal complex compounds such as azo dyes and cyanine dyes; rake pigments; carbon blacks such as carbon blacks obtained by a furnace process, a channel process or a thermal process, or acetylene black, Ketjen black or lamp black; the above-mentioned carbon blacks that have been adjusted and coated with an epoxy resin, the above-mentioned carbon blackes that have undergone a dispersion treatment in advance with a resin in a solvent and absorbed 20 to 200 mg/g of the resin, the above-mentioned carbon blacks that have undergone an acidic or alkaline surface treatment, the above-mentioned carbon blacks having an average particle size of 8 nm or more and a DBP oil absorption amount of 90 ml/100 g or less, and the above-mentioned carbon blacks having a total oxygen amount calculated from CO and $CO_2$ in the volatile components at 950° C. of 9 mg or more per 100 m² of the surface area of the carbon black; graphite, graphitized carbon black, active carbon, carbon fibers, carbon nanotube, carbon microcoil, carbon nanohorn, carbon aerogel and fullerene; aniline black, Pigment Black 7 and titanium black; hydrophobic resins, chromium oxide green, Milori blue, cobalt green, cobalt blue, manganese-based pigments, ferrocyanides, phosphate ultramarine blue, Prussian blue, ultramarine, cerulean blue, viridian, emerald green, lead sulfate, yellow lead, zinc yellow, Bengal red (red iron oxide (III)), cadmium red, synthetic iron black and amber can be used. These pigments can be used alone or by mixing plural numbers.

As the above-mentioned inorganic pigment and/or organic pigment (D), commercially available pigments can also be used, and examples may include Pigment Red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240 and 254; Pigment Orange 13, 31, 34, 36, 38, 43, 46, 48, 49, 51, 52, 55, 59, 60, 61, 62, 64, 65 and 71; Pigment Yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180 and 185; Pigment Green 7, 10 and 36; Pigment Blue 15, 15:1, 15:2, 15:3, 15:4, 15:5, 15:6, 22, 24, 56, 60, 61, 62 and 64; Pigment Violet 1, 19, 23, 27, 29, 30, 32, 37, 40 and 50, and the like.

In the colored composition of the present invention, the content of the above-mentioned inorganic pigment and/or organic pigment (D) is preferably 0 to 350 parts by mass, more preferably 0 to 250 parts by mass with respect to 100 parts by mass of the above-mentioned polymerizable compound having an ethylenically unsaturated bond (B). In the case when the content goes beyond 350 parts by mass, it is not preferable since the light transmittance of the cured product and color filter for a display device using the colored composition of the present invention, specifically the colored alkali-developable photosensitive composition, is decreased, and thus the luminance of the display device is decreased.

<Solvent (E)>

(E) a solvent can further be added to the colored composition of the present invention. Examples of the solvent may generally include solvents that can dissolve or disperse the above-mentioned respective components (the dye (A) of the present invention, and the like) as necessary, such as ketones such as methyl ethyl ketone, methyl amyl ketone, diethyl ketone, acetone, methyl isopropyl ketone, methyl isobutyl ketone, cyclohexanone and 2-heptanone; ether-based solvents such as ethyl ether, dioxane, tetrahydrofuran, 1,2-dimethoxyethane, 1,2-diethoxyethane and dipropylene glycol dimethyl ether; ester solvents such as methyl acetate, ethyl acetate, n-propyl acetate, isopropyl acetate, n-butyl acetate, cyclohexyl acetate, ethyl lactate, dimethyl succinate and texanol; cellosolve solvents such as ethylene glycol monomethyl ether and ethylene glycol monoethyl ether; alcohol solvents such as methanol, ethanol, iso- or n-propanol, iso- or n-butanol and amyl alcohol; ether ester solvents such as ethylene glycol monomethyl acetate, ethylene glycol monoethyl acetate, propylene glycol-1-monomethyl ether-2-acetate (PGMEA), dipropylene glycol monomethyl ether acetate, 3-methoxybutyl acetate and ethoxyethyl propionate; BTX solvents such as benzene, toluene and xylene; aliphatic hydrocarbon solvents such as hexane, heptane, octane and cyclohexane; terpene-based hydrocarbon oils such as turpentine oil, D-limonene and pinene; paraffin solvents such as mineral spirit, SWASOL #310 (Cosmo Matsuyama Oil Co., Ltd.) and SOLVESSO #100 (Exxon Chemical Company); halogenated aliphatic hydrocarbon solvents such as carbon tetrachloride, chloroform, trichloroethylene, methylene chloride and 1,2-dichloroethane; halogenated aromatic hydrocarbon solvents such as chlorobenzene; carbitol solvents, aniline, triethylamine, pyridine, acetate, acetonitrile, carbon disulfide, N,N-dimethylformamide, N,N-dimethylacetamide, N-methylpyrrolidone, dimethylsulfoxide, water, and the like, and these solvent can be used by one kind or as a mixed solvent of two or more kinds. Among these, ketones, ether ester solvents and the like, specifically propylene glycol-1-monomethyl ether-2-acetate, cyclohexanone and the like are preferable since they give fine compatibility between a resist and a photopolymerization initiator in a photosensitive composition.

In the colored composition of the present invention, it is preferable that the use amount of the above-mentioned solvent (E) is such that the concentration of the composition except for the solvent (E) would become 5 to 30 mass %, and in the case when the use amount is lower than 5 mass %, it is not preferable since it is difficult to thicken the film thickness and thus light at a desired wavelength light cannot be sufficiently absorbed, whereas when the use amount exceeds 30 mass %, it is not preferable since the storage property of the composition is decreased and the viscosity is increased due to the precipitation of the composition, and thus handling is decreased.

An inorganic compound can further be contained in the colored composition of the present invention. Examples of the inorganic compound may include metal oxides such as nickel oxide, iron oxide, iridium oxide, titanium oxide, zinc oxide, magnesium oxide, calcium oxide, potassium oxide, silica and alumina; layered clay mineral, Milori blue, calcium carbonate, magnesium carbonate, cobalt systems, manganese systems, glass powder, mica, talc, kaolin, ferrocyanides, various metal sulfates, sulfides, selenides, aluminum silicate, calcium silicate, aluminum hydroxide, platinum, gold, silver, copper and the like, and among these, titanium oxide, silica, layered clay mineral, silver and the like are preferable. In the colored composition of the present invention, the content of the inorganic compound is preferably 0.1 to 50 parts by mass, more preferably 0.5 to 20 parts by mass with respect to 100 parts by mass of the above-mentioned polymerizable compound having an ethylenically unsaturated bond (B), and these inorganic compounds can be used by one kind or two or more kinds.

These inorganic compounds are used as, for example, fillers, antireflective agents, conductant agents, stabilizers, flame retarders, agents for improving mechanical strength, agents for absorbing special wavelength, ink repellants and the like.

In the colored composition of the present invention, in the case when the pigment and/or inorganic compound is/are used, a dispersing agent can be added. The dispersing agent may be any one as long as it can disperse and stabilize color materials and inorganic compounds, and commercially available dispersing agents such as BYK series manufactured by BYK-Chemie GmbH can be used, and polyesters having a basic functional group, polymer dispersing agents composed of a polyether or a polyurethane, and dispersing agents having a nitrogen atom as a basic functional group, wherein the functional group having a nitrogen atom is an amine and/or a quartenary salt thereof, and having an amine value of 1 to 100 mgKOH/g, are preferably used.

Furthermore, where necessary, conventionally-used additives such as thermal polymerization inhibitors such as p-anisole, hydroquinone, pyrocatechol, t-butylcatechol and phenothiazine; plasticizers; adhesion promoters; fillers; defoaming agents; leveling agents; surface adjusting agents; antioxidants; ultraviolet absorbers; dispersion aids; flocculation inhibitors; catalysts; effect promoters; crosslinking agents; and thickeners can be added to the colored composition of the present invention.

In the colored composition of the present invention, although the content of optional components other than the dye (A) of the present invention, polymerizable compound having an ethylenic ally unsaturated bond (B) and photopolymerization initiator (C) (however, the inorganic pigment and/or organic pigment (D), and the solvent (E) are excluded) is suitably selected depending on the purpose of use thereof and not specifically limited, the content is preferably 50 parts by mass or less in total with respect to 100 parts by mass of the above-mentioned polymerizable compound having an ethylenically unsaturated bond (B).

Furthermore, it is also possible to improve the property of the cured product formed of the colored composition of the present invention, by using other organic polymer together with the above-mentioned polymerizable compound having an ethylenically unsaturated bond (B). Examples of the above-mentioned organic polymer may include polystyrene, polymethyl methacrylate, methyl methacrylate-ethyl acrylate copolymers, poly(meth)acrylic acid, styrene-(meth)acrylic acid copolymers, (meth)acrylic acid-methyl methacrylate copolymers, ethylene-vinyl chloride copolymers, ethylene-vinyl copolymers, polyvinyl chloride resins, ABS resins, nylon 6, nylon 66, nylon 12, urethane resins, polycarbonate polyvinyl butyral, cellulose esters, polyacrylamide, saturated polyesters, phenolic resins, phenoxy resins, polyamideimide resins, polyamic acid resins, epoxy resins and the like, of which polystyrene, (meth)acrylic acid-methyl methacrylate copolymers and epoxy resins are preferable.

In the case when the other organic polymer is used, the use amount thereof is preferably 10 to 500 parts by mass with respect to 100 parts by mass of the above-mentioned polymerizable compound having an ethylenically unsaturated bond (B).

In the colored composition of the present invention, monomers having an unsaturated bond, chain transfer agents, sensitizers, surfactants, silane coupling agents, melamines and the like can further be used in combination.

Examples of the above-mentioned monomer having an unsaturated bond may include 2-hydroxyethyl acrylate, 2-hydroxypropyl acrylate, isobutyl acrylate, n-octyl acrylate, isooctyl acrylate, isononyl acrylate, steryl acrylate, methoxyethyl acrylate, dimethylaminoethyl acrylate, zinc acrylate, 1,6-hexanediol diacrylate, trimethylolpropane triacrylate, 2-hydroxyethyl methacrylate, 2-hydroxypropyl methacrylate, butyl methacrylate, t-butyl methacrylate, cyclohexyl methacrylate, trimethylolpropane trimethacrylate, dipentaerythritol pentaacrylate, dipentaerythritol hexaacrylate, pentaerythritol tetraacrylate, pentaerythritol triacrylate, bisphenol A diglycidyl ether(meth)acrylate, bisphenol F diglycidyl ether(meth)acrylate, bisphenol Z diglycidyl ether (meth)acrylate, tripropylene glycol di(meth)acrylate and the like.

As the above-mentioned chain transfer agents and sensitizers, sulfur atom-containing compounds are generally used. Examples may include mercapto compounds such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotine acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl(4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercaptobenzoimidazole, 2-mercapto-3-pyridinol, 2-mercaptobenzothiazole, mercaptoacetate, trimethylolpropane tris(3-mercaptopropionate) and pentaerythritol tetrakis(3-mercaptopropionate), disulfide compounds obtained by oxidizing the mercapto compounds, alkyl iodide compounds such as iodo acetate, iodo propionate, 2-iodoethanol, 2-iodoethanesulfonic acid and 3-iodopropanesulfonic acid, aliphatic multifunctional thiol compounds such as trimethylolpropane tris(3-mercaptoisobutyrate), butanediol bis(3-mercaptoisobutyrate), hexanedithiol, decanedithiol, 1,4-dimethylmercaptobenzene, butanediol bisthiopropionate, butanediol bisthioglycolate, ethylene glycol bisthioglycolate, trimethylolpropane tristhioglycolate, butanediol bisthiopropionate, trimethylolpropane tristhiopropionate, trimethylolpropane tristhioglycolate, pentaerythritol tetrakisthiopropionate, pentaerythritol tetrakisthioglycolate, trishydroxyethyl tristhiopropionate, the following compound No. 125 and trimercaptopropionic acid tris(2-hydroxyethyl)isocyanurate, KARENZ MT BD1, PE1 and NR1 manufactured by Showa Denko K. K., and the like.

[Chemical Formula 37]

Compound No. 125

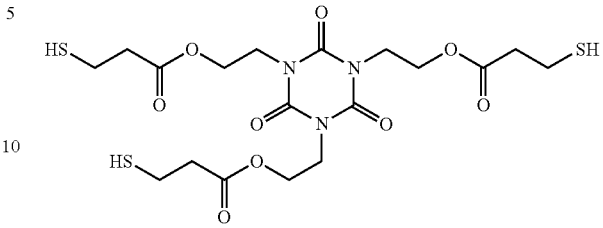

As the above-mentioned surfactants, surfactants such as fluorine surfactants such as perfluoroalkylphosphate esters and perfluoroalkylcarboxylate salts, anion surfactants such as alkali salts of higher aliphatic acids, alkylsulfonates salts and alkylsulfate salts, cation surfactants such as higher amine halogenate salts and quaternary ammonium salts, nonionic surfactants such as polyethylene glycol alkyl ethers, polyethylene glycol aliphatic acid esters, sorbitan aliphatic acid esters and aliphatic acid monoglycerides, amphoteric surfactants, and silicone surfactants can be used, and these may be used in combination.

As the above-mentioned silane coupling agents, for example, silane coupling agents manufactured by Shin-Etsu Chemical Co., Ltd. can be used, and among these, KBE-9007, KBM-502, KBE-403 and the like, and silane coupling agents having an isocyanate group, a methacryloyl group or an epoxy group are preferably used.

Examples of the above-mentioned melamine compounds may include compounds in which whole or a part of (at least two) active methylol groups ($CH_2OH$ groups) in a nitrogen compound are alkyl-etherified such as (poly)methylolmelamine, (poly)methylolglycoluril, (poly)methylolbenzoguanamine and (poly)methylolurea. Examples of the alkyl groups that constitute the alkyl ethers may include a methyl group, an ethyl group or a butyl group, and the alkyl groups may be the same or different from each other. Furthermore, the methylol groups that are not alkyl-etherified may be self-condensed in one molecule, or may be condensed between two molecules to thereby form an oligomer component. Specifically, hexamethoxymethylmelamine, hexabutoxymethylmelamine, tetramethoxymethylglycoluril, tetrabutoxymethylglycoluril and the like can be used. Among these, alkyl-etherified melamines such as hexamethoxymethylmelamine and hexabutoxymethylmelamine are preferable.

The colored composition of the present invention can be applied to support bases such as soda glass, quartz glass, semiconductor substrates, metals, paper and plastics by known means such as a spin coater, a roll coater, a bar coater, a die coater, a curtain coater, various printings and immersion. Alternatively, the colored composition of the present invention can also be applied once to a support base such as a film and then transferred to other support base, and the method for the application is not limited.

Furthermore, as a light source of active light used for curing the colored composition of the present invention, a light source that emits light at a wavelength of 300 to 450 nm can be used, and for example, ultrahigh pressure mercury, mercury vapor arc, carbon arc, xenone arc and the like can be used.

Furthermore, a laser direct drawing process that forms an image directly from digital information from a computed or the like by using laser light as a light source for exposing without using a mask is useful since not only producibility but also resolution and position accuracy can be improved, and as the laser light therefor, light at a wavelength of 340 to 430 nm is preferably used, and laser lights that emit light from the visible to infrared region such as argon ion laser, helium-neon laser, YAG laser and semiconductor laser are also used. In the cases when these lasers are used, a sensitizing pigment that absorbs the visible to infrared region is added.

The colored composition of the present invention (or a cured product thereof) can be used for various uses such as photocurable coating materials or varnishes, photocurable adhesives, printed substrates, or color filters in liquid crystal display panels for color display in color TV sets, PC monitors, handheld terminals, digital cameras and the like, color filters for CCD image sensors, electrode materials for plasma display panels, powder coating, printing inks, printing plates, adhesives, dental compositions, resins for stereolithography, gel coats, photoresists for electronics, resists for electrical plating, etching resists, both liquid and dried films, solder resists, resists for producing color filters for uses in various displays or for forming structures in the production steps of plasma display panels, electroluminescent display devices and LCDs, compositions for enclosing electric and electronic parts, solder resists, magnetic recording materials, minute mechanical parts, waveguides, light switches, masks for plating, etching masks, color test systems, glass fiber cable coatings, stencils for screen printing, materials for producing three-dimensional objects by stereolithography, materials for holographic recording, image recording materials, fine electronic circuits, decoloring materials, decoloring materials for image recording materials, decoloring materials for image recording materials using microcapsules, photoresist materials for printed wiring boards, photoresist materials for UV and visible laser direct image systems, photoresist materials for use in formation of dielectric layers in sequential lamination of printed circuit substrates or protective films, and the uses are not specifically limited.

The colored composition of the present invention (specifically, the colored alkali-developable photosensitive composition) is used for the purpose of forming pixels of color filters, and is specifically useful as a photosensitive composition for forming color filters for display devices for image display devices such as liquid crystal display panels.

Furthermore, in the case when the compound represented by the above-mentioned general formula (1) is used alone in the dye (A) of the present invention, the colored composition of the present invention becomes a yellow optical element. The color filter for a display device of the present invention may have optical elements of red, green, blue, orange, purple and black besides the cured product of the present invention.

The above-mentioned color filter for a display device is preferably formed by (1) a step of forming a coating of the colored composition of the present invention (specifically, the colored alkali-developable photosensitive composition) on a substrate, (2) a step of irradiating the coating with active light through a mask having a predetermined pattern shape, (3) a step of developing the exposed coating by a developer liquid (specifically, an alkali developer liquid), and (4) a step of heating the developed coating. Furthermore, the colored composition of the present invention is also useful as a colored composition for an inkjet process and a transfer process, which do not include a step of developing.

The production of the color filter used for a liquid crystal display panel or the like can be prepared by repetitively conducting the steps of the above-mentioned (1) to (4) by using the colored composition of the present invention or other colored composition, and combining patterns of two or more colors.

EXAMPLES

Hereinafter the present invention will further be explained in detail with referring to Examples and the like, but the present invention is not construed to be limited by these Examples and the like.

Examples 1-1 to 1-4 show the synthesis examples of the novel compounds of the present invention (the dyes of the present invention), Comparative Examples 1-1 and 1-2 show the synthesis examples of comparative compounds (comparative dyes); in Evaluation Example 1, the heat-resistances of the novel compounds of the present invention and comparative compounds obtained in Examples 1-1 to 1-4 and Comparative Examples 1-1 and 1-2 were evaluated; and in Evaluation Example 2, the absorption wavelength properties of the novel compounds of the present invention and comparative compounds obtained in Examples 1-1 to 1-4 and Comparative Examples 1-1 and 1-2 were evaluated.

Examples 2-1 to 2-3 and Comparative Example 2-1 shows the preparation examples of the colored alkali-developable photosensitive compositions of the present invention and for comparison; and in Evaluation Examples 3-1 to 3-3 and Comparative Evaluation Example 1, the heat-resistances of the colored alkali-developable photosensitive compositions of the present invention and for comparison obtained in Examples 2-1 to 2-3 and Comparative Example 2-1 were evaluated.

Example 1-1

Synthesis of Compound No. 1

Bis(4-formylphenyl)phenylamine (0.90 g, 3 mmol), ethyl cyanoacetate (0.75 g, 6.6 mmol) and ethanol (1.26 g) were added to a reaction container and heated to 50° C. under stirring. Triethylamine (0.06 g, 0.6 mmol) was then added dropwise, a reaction was conducted at 50° C. for 2 hours, and the reactant was cooled to room temperature. The reaction solution was subjected to liquid separation with ethyl acetate/water, the organic layer was dried under a reduced pressure, and the precipitated solid was washed with hexane to thereby give 1.13 g (yield 95.2%) of a yellow powder. That the obtained yellow powder was the intended substance was confirmed by $^1$H-NMR and IR. Furthermore, the solubility and absorption wavelength properties (absorption wavelength $\lambda_{max}$ and absorption coefficient e) of compound No. 1 were measured. PGMEA was added dropwise to 0.1 g of the compound under stirring, and the solubility was defined as the concentration at the time when PGMEA had completely dissolved the compound. Furthermore, the absorption wavelength properties were measured in a CHCl$_3$ solution. These results are shown in [Table 1] to [Table 3].

Example 1-2

Synthesis of Compound No. 2

Tris(4-formylphenyl)amine (0.99 g, 3 mmol), ethyl cyanoacetate (1.09 g, 9.6 mmol) and ethanol (1.84 g) were added to a reaction container and heated to 50° C. under stirring. Thereafter triethylamine (0.06 g, 0.6 mmol) was added dropwise, a reaction was conducted at 50° C. for 2 hours, and the reactant was cooled to room temperature. The precipitated solid was separated by filtration, and recrystallized by ethyl acetate/ethanol to thereby give 1.30 g (yield: 72.2%) of a yellow crystal. That the obtained yellow crystal was the intended substance was confirmed by $^1$H-NMR and IR. Furthermore, the solubility and absorption wavelength properties of compound No. 2 were measured in a similar manner to Example 1-1. These results are shown in [Table 1] to [Table 3].

Example 1-3

Synthesis of Compound No. 5

4,4'(piperidine-1,4-diyl)dibenzaldehyde (1.8 g, 7 mmol), ethyl cyanoacetate (1.58 g, 14 mmol) and ethanol (3.4 g) were put into a reaction container and mixed. Thereafter triethylamine (0.06 g, 0.6 mmol) was added dropwise to the reaction solution under stirring at room temperature, and after completion of the dropwise addition, a reaction was conducted under reflux for 2 hours. After completion of the reaction, the reactant was cooled to room temperature, and the precipitated solid was separated by filtration and recrystallized by dimethylformamide/methanol to thereby give 1.0 g (yield: 29.4%) of a yellow crystal. That the obtained yellow crystal was the intended substance was confirmed by $^1$H-NMR and IR. Furthermore, the solubility and absorption wavelength properties of compound No. 5 were measured in a similar manner to Example 1-1. These results are shown in [Table 1] to [Table 3].

Example 1-4

Synthesis of Compound No. 46

4,4'-(hexane-1,6-diylbis(ethylazanediyl)dibenzaldehyde (2.66 g, 7 mmol), ethyl cyanoacetate (1.58 g, 14 mmol) and ethanol (3.4 g) were put into a reaction container and heated to 50° C. under stirring. Thereafter triethylamine (0.06 g, 0.6 mmol) was added dropwise, a reaction was conducted at 50° C. for 2 hours, and the reactant was cooled to room temperature. The precipitated solid was separated by filtration, and recrystallized by ethyl acetate/ethanol to thereby give 2.1 g (yield: 52.5%) of a yellow crystal. That the obtained yellow crystal was the intended substance was confirmed by $^1$H-NMR and IR. Furthermore, the solubility of compound No. 46 was measured in a similar manner to Example 1-1. These results are shown in [Table 1] to [Table 3].

TABLE 1

| | Chemical shift ppm (proton number, multiplicity), |
|---|---|
| Compound No. 1 (CDCl$_3$) | 1.40(6H, t), 4.37(4H, q), 7.13-7.43(11H, m), 7.91(4H, d), 8.14(2H, s) |
| Compound No. 2 (CDCl$_3$) | 1.41(9H, t), 4.38(6H, q), 7.24(6H, d), 7.96(6H, d), 8.18(3H, s) |
| Compound No. 5 (DMSO) | 1.28(6H, t), 3.68(8H, t), 4.26(4H, q), 7.06(4H, d), 7.99(4H, d), 8.14(2H, s) |
| Compound No. 46 (CDCl$_3$) | 1.23(6H, t), 1.35(6H, t), 1.47(4H, m), 1.66(4H, m), 3.36(4H, q), 3.46(4H, q) 4.34(4H, q), 6.62(4H, d), 7.91(4H, d), 8.04(2H, s) |

TABLE 2

| | IR Absorption Spectrum/cm$^{-1}$ |
|---|---|
| Compound No. 1 | 2983, 2220, 1717, 1575, 1502, 1435, 1367, 1330, 1265, 1210, 1177, 1088, 1015, 823, 762, 698, 507 |

TABLE 2-continued

| | IR Absorption Spectrum/cm$^{-1}$ |
|---|---|
| Compound No. 2 | 2983, 2220, 1717, 1575, 1502, 1435, 1367, 1330, 1265, 1210, 1177, 1088, 1015, 833, 761, 698, 507 |
| Compound No. 5 | 2901, 2212, 1690, 1604, 1564, 1505, 1447, 1409, 1362, 1332, 1269, 1224, 1174, 1078, 1025, 996, 943, 809, 758, 718, 606, 579 |
| Compound No. 46 | 2931, 2112, 1702, 1607, 1555, 1507, 1479, 1438, 1407, 1317, 1349, 1308, 1273, 1226, 1183, 1161, 1093, 1067, 1025, 987, 853, 825, 760, 731, 585 |

TABLE 3

| | solubility/wt % |
|---|---|
| Compound No. 1 | 4.6 |
| Compound No. 2 | 3.5 |
| Compound No. 5 | 0.1 |
| Compound No. 46 | 0.5 |

Comparative Example 1-1

Synthesis of Comparative Compound No. 1

The following Comparative compound No. 1 was obtained by the method described in paragraph [0046] of the above-mentioned Patent Literature 4 (JP 2007-286189 A).

Comparative Example 1-2

Synthesis of Comparative Compound No. 2

4'-(N,N-diethylamino)acetophenone (3.55 g, 20 mmol) and 2-ethoxyethyl cyanoacetate (3.77 g, 24 mmol) were dispersed in ethanol (6.33 g) and heated to 50° C. under stirring. Triethylamine (0.2 g, 2 mmol) was added dropwise thereto and reacted at 70° C. for 3 hours. The reactant was cooled and then subjected to oil-water separation by using ethyl acetate/ion-exchanged water, and the obtained organic phase was distilled off under a reduced pressure to thereby give 4.3 g of a crude product. The crude product was recrystallized by a mixed solution of ethyl acetate/hexane and dried to thereby give the following Comparative compound No. 2 (an orange crystal, yield amount: 2.2 g and yield: 34.8%).

[Chemical Formula 38]

Comparative compound No. 1

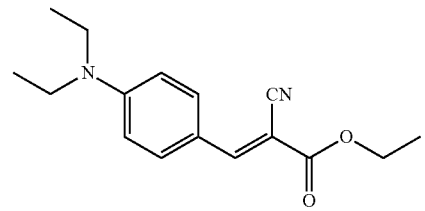

-continued

Comparative compound No. 2

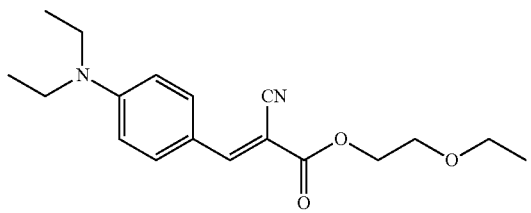

Evaluation Example 1

Evaluation of Heat-Resistance by TG-DTA

Compounds Nos. 1, 2, 5 and 46 and Comparative Compounds Nos. 1 and 2 obtained above were analyzed by TG-DTA to thereby measure the melting points and temperatures at 10% weight loss. The results are shown in [Table 4].

TABLE 4

|  | melting point/° C. | temperatures at 10% weight loss/° C. |
| --- | --- | --- |
| Compound No. 1 | — | 355 |
| Compound No. 2 | 168 | 370 |
| Compound No. 5 | 308 | 345 |
| Compound No. 46 | 124 | 346 |
| Comparative Compound No. 1 | 97 | 259 |
| Comparative Compound No. 2 | 80 | 252 |

It is apparent from the results in the above-mentioned [Table 4] that the dye (A) of the present invention containing the compound represented by the above-mentioned general formula (1) has high heat-resistance.

Evaluation Example 2

Evaluation of Absorption Wavelength Property

The maximum absorption wavelengths of Compounds Nos. 1, 2, 5 and 46 and Comparative Compounds Nos. 1 and 2 obtained above were each evaluated in a $CHCl_3$ solution. The results are shown in [Table 5].

TABLE 5

|  | λmax/nm |
| --- | --- |
| Compound No. 1 | 460 |
| Compound No. 2 | 452 |
| Compound No. 5 | 423 |
| Compound No. 46 | 430 |
| Comparative Compound No. 1 | 430 |
| Comparative Compound No. 2 | 432 |

It is apparent from the results in the above-mentioned [Table 5] that the dye (A) of the present invention containing the compound represented by the above-mentioned general formula (1) has a suitable absorption wavelength.

Example 2-1

Preparation of Colored Alkali-Developable Photosensitive Composition No. 1

<Step 1> Preparation of Alkali-Developable Photosensitive Composition No. 1

30.33 g of ACA Z250 (manufactured by Daicel-Cytec Company Ltd.) and 11.04 g of ARONIX M-450 (manufactured by Toagosei Co., Ltd.) as the component (B), 1.93 g of IRGACURE 907 (manufactured by BASF) as the component (C), 36.60 g of PGMEA and 20.08 g of cyclohexanone as the component (E), and 0.01 g of FZ2122 (manufactured by Dow Corning Toray Co., Ltd.) as other component were mixed, and stirred until the insoluble substances disappeared to thereby give alkali-developable photosensitive composition No. 1.

<Step 2> Dye Solution No. 1

1.90 g of dimethylacetamide was added to 0.10 g of compound No. 1 that was obtained above as the component (A), and dissolved by stirring to thereby give dye solution No. 1.

<Step 3> Preparation of Colored Alkali-Developable Photosensitive Composition No. 1

5.0 g of the alkali-developable photosensitive composition No. 1 obtained in Step 1 and 1.0 g of the dye solution No. 1 obtained in Step 2 were mixed and stirred until the mixture became homogeneous to thereby give colored alkali-developable photosensitive composition No. 1 of the present invention.

Example 2-2

Preparation of Colored Alkali-Developable Photosensitive Composition No. 2

Colored alkali-developable photosensitive composition No. 2 was obtained in a similar manner to that of Example 2-1, except that compound No. 1 as the component (A) in Step 2 of Example 2-1 was changed to compound No. 2 obtained above.

Example 2-3

Preparation of Colored Alkali-Developable Photosensitive Composition No. 3

Colored alkali-developable photosensitive composition No. 3 was obtained in a similar manner to that of Example 2-1, except that compound No. 1 as the component (A) in Step 2 of Example 2-1 was changed to compound No. 46 obtained above.

Comparative Example 2-1

Preparation of Comparative Colored Alkali-Developable Photosensitive Composition No. 1

Comparative colored alkali-developable photosensitive composition No. 1 was obtained in a similar manner to that of Example 2-1, except that compound No. 1 as the component (A) in Step 2 of Example 2-1 was changed to comparative compound No. 1.

Evaluation Examples 3-1, 3-2 and 3-3, and
Comparative Evaluation Example 1

Evaluation of Heat-Resistance by Calcination

The colored alkali-developable photosensitive compositions No. 1, No. 2 and No. 3 obtained above, and comparative colored alkali-developable photosensitive composition No. 1 were each applied to a glass substrate under conditions of 410 rpm × 7 sec, and dried on a hot plate (90° C., 90 sec). The obtained coating was exposed to light by a ultrahigh pressure mercury lamp (150 mJ/cm²). The coating after the exposure to light was calcined under conditions of 230° C.×30 min. The absorbance of the coating before the calcination (after the exposure to light) and the absorbance of the coating after the calcination at the maximum absorption wavelength (λmax) of the compound (dye) as used were measured, and considering the absorption of the coating before the calcination (after the exposure to light) as 100, the absorbance of the coating after the calcination closer to 100 was evaluated to give higher heat-resistance. The results are shown in [Table 6].

TABLE 6

| | | | relative intensity | |
|---|---|---|---|---|
| | | λmax/ nm | after the exposure | 230° C., 30 min |
| Evaluation Example 3-1 | Compound No. 1 | 458 | 100 | 94.9 |
| Evaluation Example 3-2 | Compound No. 2 | 452 | 100 | 98.5 |
| Evaluation Example 3-3 | Compound No. 46 | 436 | 100 | 99.9 |
| Comparative Evaluation Example 1 | Comparative Compound No. 1 | 430 | 100 | 12.5 |

It is apparent from the results in the above-mentioned [Table 6] that the colored alkali-developable photosensitive composition of the present invention has high heat-resistance.

According to the above-mentioned results, it is obvious that a dye using the novel compound of the present invention is excellent in absorption wavelength and heat-resistance, and it is also obvious that a colored composition and a cured product thereof using this dye has high heat-resistance, and thus the dye and colored composition of the present invention are useful for color filters for display devices.

The invention claimed is:

1. A colored photosensitive composition, comprising:

(A) a dye containing at least one kind of compound represented by general formula (1), (B) a polymerizable compound having an ethylenically unsaturated bond, and (C) a photopolymerization initiator,

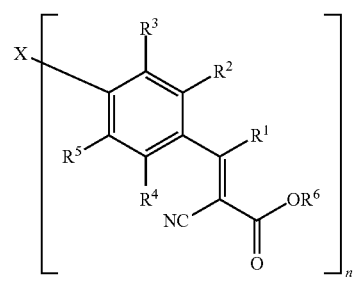

(1)

wherein
$R^1$ represents a hydrogen atom, a methyl group, a phenyl group or a cyano group,
$R^2$ to $R^5$ each independently represents a hydrogen atom, a halogen atom, a cyano group, a hydroxyl group, a nitro group, an alkyl group having 1 to 8 carbon atom(s), an alkoxy group having 1 to 8 carbon atom(s), a halogenated alkyl group having 1 to 8 carbon atom(s) or a halogenated alkoxy group having 1 to 8 carbon atom(s), wherein $R^2$ and $R^3$, and $R^4$ and $R^5$ may be respectively connected to each other to form a ring structure,
$R^6$ represents a hydrogen atom, an alkyl group having 1 to 8 carbon atom(s) or an aromatic hydrocarbon group optionally having substituent(s) having 6 to 35 carbon atoms, wherein the alkyl group may be interrupted by —COO—, —O—, —OCO—, —NHCO—, —NH— or —CONH—,
n represents an integer of 2 to 6,
X represents a nitrogen atom, —NR¹⁰—, an oxygen atom, a sulfur atom, —SO—, —SO₂—, a phosphorus atom, —PR¹⁰—, or a substituent having 1 to 35 carbon atom(s) having a similar valency number to that of n,
$R^{10}$ represents a hydrogen atom, an alkyl group having 1 to 8 carbon atom(s), an aryl group having 6 to 20 carbon atoms or an arylalkyl group having 7 to 20 carbon atoms, wherein the alkyl group, aryl group and aryl alkyl group may be substituted with a halogen atom, a hydroxyl group, a nitro group or a cyano group, the alkyl group may be interrupted by —COO—, —O—, —OCO—, —NHCO—, —NH— or —CONH—, and $R^3$ and X, and $R^5$ and X may be respectively connected to each other to form a ring structure.

2. The colored photosensitive composition according to claim 1, which is a colored alkali developable photosensitive composition, wherein (B) the polymerizable compound having an ethylenically unsaturated bond is (B') an alkali developable polymerizable compound having an ethylenically unsaturated bond.

3. The colored photosensitive composition according to claim 1, further comprising an inorganic pigment and/or an organic pigment (D).

4. The colored photosensitive composition according to claim 2, further comprising an inorganic pigment and/or an organic pigment (D).

5. A cured product of the colored photosensitive composition according to claim 1.

6. A cured product of the colored photosensitive composition according to claim 2.

7. A color filter for a display device, which is formed by using the cured product according to claim 5.

8. A color filter for a display device, which is formed by using the cured product according to claim 6.

9. A liquid crystal display panel, which is formed by using the color filter for a display device according to claim 7.

10. A liquid crystal display panel, which is formed by using the color filter for a display device according to claim 8.

* * * * *